US005908760A

United States Patent [19]
Bojsen et al.

[11] Patent Number: 5,908,760
[45] Date of Patent: Jun. 1, 1999

[54] α-1,4-GLUCAN LYASE FROM A FUNGUS, ITS PURIFICATION GENE CLONING AND EXPRESSION IN MICROORGANISMS

[75] Inventors: Kirsten Bojsen, Allerod, Denmark; Shukun Yu, Malmo, Sweden; Karsten Kragh, Viby J; Tove Christensen, Allerod, both of Denmark; Jan Marcussen, Copenhagen, Denmark

[73] Assignee: Danisco A/S, Copenhagen, Denmark

[21] Appl. No.: 08/633,770

[22] PCT Filed: Oct. 15, 1994

[86] PCT No.: PCT/EP94/03398

§ 371 Date: Jul. 8, 1996

§ 102(e) Date: Jul. 8, 1996

[87] PCT Pub. No.: WO95/10617

PCT Pub. Date: Apr. 20, 1995

[30] Foreign Application Priority Data

Oct. 15, 1993 [GB] United Kingdom .................... 9321302

[51] Int. Cl.⁶ .............................. C12N 15/00; C12N 9/88; C07H 21/04
[52] U.S. Cl. .................. 435/69.1; 536/23.74; 536/24.32; 435/183; 435/200; 435/232; 530/344; 530/350; 530/823; 935/11; 935/14; 935/68
[58] Field of Search ................................ 435/69.1, 240.1, 435/320.1, 183, 200, 232; 536/23.74, 24.32; 935/11, 14, 66, 68; 530/344, 350, 412, 417, 820, 823

[56] References Cited

FOREIGN PATENT DOCUMENTS 2617502  6/1987  France .

OTHER PUBLICATIONS

Yu, Shukun, et al.; Biochimica et Biophysuca Acta, 1156(1993) 313–320; *a–1, 4–Glucan lyase, a new class of starch/glycogen degrading enzyme. I. Efficient purification and characterization from red seaweeds.*
Pall, Martin L., et al.; Fungal Genetics Newsletter; pp. 58–63; *The use of Ignite (Basta;glufosinate;phosphinothricin) to select transformants of bar–containing plasmids in Neurospora crassa.*
Punt, Peter J., et al.; Fungal Transformation Using Dominant Selection; Methods in Enzymology, vol. 216; 1992; pp. 447–449; *Transformation of Filamentous Fungi Based on Mygromycin B and Phleomycin Resistance Markers.*
Archer, David B., et al.; Biotechnology Letters, vol. 14, No. 5 (May 1992) pp. 357–362; *Proleolytic Degradation of Heterologous Proteins Expressed in Aspergillus Niger.*
Punt, Peter J., et al.; Biotechnology, 17 (1991) 19–33; *Intracellular and extracellular production of proteins in Aspergillus under the control of expression signals of the highly expressed Aspergillus nidulans gpdA gene.*
Daboussi, M.J., et al.; Current Genetics, 1989; 15: 453–456; Short communications; *Transformation of seven species of filamentous fungi using the nitrate reductase gene of Aspergillus nidulans.*

Dellaporta, Stephen L., et al.; Plant Molecular Biology Reporter; vol. 1, No. 4, Fall 1983; pp. 19–21; *A Plant DNA Minipreparation: Version II.*
Barkholt, Vibeke, et al.; Analytical Biochemistry 177, 318–211, pp. 318–322 (1989); *Amino Acid Analysis: Determination of cysteine plus Half–Cystine in Proteins after Hydrochloric Acid Hydrolysis with a Disulfide Compound as Additive.*
Sanger et al., "DNA sequencing with Chain–Terminating inhibitors," *Proc National Academy Science*, USA vol. 74, pp. 5463–5467 (1979).
Dellaporta et al., "A plant DNA minipreparation: Version II," *Plant Molecular Biology Reporter*, vol. 1, pp. 19–21 (1983).
Buxton et al., "Transformation of *Aspergillus niger* using the argB Gene of *Aspergillus nidulans*," *Gene*, vol. 37, pp. 207–214 (1985).
Baute et al., "Fungal enzymic activity degrading 1,4–x–D–Glucans to 1,5–D–Anhydrofructose" *Phytochemistry*, vol. 27, No. 11, pp. 3401–3403 (1988).
Punt et al., "Intracellular and extracellular production of proteins in Aspergillus under . . ." *Journal of Biotechnology*, vol. 17, pp. 19–34 (1991).
Archer et al., "Proteolytic degradation of Heterologous proteins expressed in . . . ," *Biotechnology Letters*, vol. 14, No. 5, pp. 357–362 (1992).
Punt et al., "Transformation of Filamentous fungi based on Hygromysin B and Phleomycin . . . ," *Methods of Enzymology*, vol. 216, pp. 447–457 (1992).
Pall et al., "The use of ignite to select transformants of bar containing plasmids in . . . ," *Fungal Genetics Newsletter*, vol. 40, pp. 59–62 (1993).
Plant Physiology, Biochemistry and Biophysics, Bio. Abstr. 57: AB–926, No. 52735, referencing Baute et al., Phytochemistry, 27:3401–3404 (1988).
Baute, et al., Phytochemistry, *"Fungal Enzymic Activity Degrading 1,4–a–D–Glucans to 1,5,–D–Anhydrofructose,"* 27:3401–3403 (1988).
Baute, et al., Bull. Soc. Pharm. Bordeaux, "Bioconversions Fongiques Produisant, A Partr De Sucres, Des Composes Pyrontiques Inhabituels A Activite Antibiotique," 128:9–18 (1989).
Shukun Yu and Marianne Pedersen, Planta, *"a–1,4, Glucan lyase, a new class of starch/glycogen–degrading enzyme,"* 191:137–143, (1993).
Yu et al, Planta (1993) 191:137–142.
Baute et al, Phytochemistry (1988) vol. 27:3401–3403.
Kriegler, Gene Transfer & Expression, Stockton Press, NY, NY, 1990 pp. 114–132.
Yu et al, Biochimica of Biophys Acta (1993)1156: 313–320.
Lee et al, Science (1988)239:1288–1291.

*Primary Examiner*—Carla J. Myers
*Attorney, Agent, or Firm*—Knobbe Martens Olson & Bear LLP

[57]  ABSTRACT

A method of preparing -glucan lyase enzymes is described. The method comprises isolating the enzymes from a culture of fungus wherein the culture is substantially free of any other organisms. Also described are the amino acid sequences for the enzymes and their coding sequences.

12 Claims, 13 Drawing Sheets

```
       10         20         30         40         50         60
        |          |          |          |          |          |
   1 AGACAGGTGC GTTTTTGTTT ATTCTATTCT GTGCGGCAGA TATGCACTCA CAAGAAACAA
  61 ATTGTACAAA TATTTCTAAT TACAGTTGTA GGTGCAGTTG AAAATCCGGT CGCACAAAGA
 121 TCATTGATGC ACAAAGATGA TAACGCCTGA TTAGTACTCA AGGTTTAATT GGGTATGTGT
 181 GCGACCTCTC TTTGGCTAGC ATTACCTGAT TGGTTACAAC TGCAAATACT GCGGCAGCAA
 241 TGAGGAATGA AGTCAGCATC GATAGCTCGG CCTCATAAAA ATTGATTTCA ATTTTATATT
 301 CCCAGTTTTA ATCTCGAATC CTATATAATG GCCATCGTTC CCTCCTCGCC TCTTCATTCT
 361 CCTCCATCAC TCCAGCTCAG TCATCCCTCA ACTTGGCCTC CTCTGATATC TTCCGAACAA
 421 AACATCTTGT CCAATCTTTT TTTGAGCTAG ATCTCATTAT ACCTCCGTCA TGGCAGGATT
 481 TTCTGATCCT CTCAACTTTT GCAAAGCAGA AGACTACTAC AGTGTTGCGC TAGACTGGAA
 541 GGGCCCTCAA AAAATCATTG GAGTAGACAC TACTCCTCCA AAGAGCACCA AGTTCCCCAA
 601 AAACTGGCAT GGAGTGAACT TGAGATTCGA TGATGGGACT TTAGGTGTGG TTCAGTTCAT
 661 TAGGCCGTGC GTTTGGAGGG TTAGATACGA CCCTGGTTTC AAGACCTCTG ACGAGTATGG
 721 TGATGAGAAT ACGTGAGTTA CCCCATATGT CATTATTGGT AGCGAAAAAC ATATGCTAAT
 781 CAACTAACGA GGCATATAGG AGGACAATTG TGCAAGATTA TATGAGTACT CTGAGTAATA
 841 AATTGGATAC TTATAGAGGT CTTACGTGGG AAACCAAGTG TGAGGATTCG GGAGATTTCT
 901 TTACCTTCTC AGTAAGTGCC AGTACTGCTA TAGCTCCGCT ATATATATAA CACCACTAAC
 961 TAACTGCCCT AAATAGTCCA AGGTCACCGC CGTTGAAAAA TCCGAGCGGA CCCGCAACAA
1021 GGTCGGCGAT GGCCTCAGAA TTCACCTATG GAAAAGCCCT TTCCGCATCC AAGTAGTGCG
1081 CACCTTGACC CCTTTGAAGG ATCCTTACCC CATTCCAAAT GTAGCCGCAG CCGAAGCCCG
1141 TGTGTCCGAC AAGGTCGTTT GGCAAACGTC TCCCAAGACA TTCAGAAAGA ACCTGCATCC
1201 GCAACACAAG ATGCTAAAGG ATACAGTTCT TGACATTGTC AAACCTGGAC ATGGCGAGTA
1261 TGTGGGGTGG GGAGAGATGG GAGGTATCCA GTTTATGAAG GAGCCAACAT TCATGAACTA
1321 TTTTAGTAAG CCCCGAAGAG GTTCCTTATA AATTCTTGGT GGTCATTTTT ACTAACCCAG
1381 TGTAGACTTC GACAATATGC AATACCAGCA AGTCTATGCC CAAGGTGCTC TCGATTCTCG
1441 CGAGCCACTG TAAGTACCGT CCTGTGGCAC GACTTAACCC AATAACTAAT CTTTCAACAA
1501 GGTACCACTC GGATCCCTTC TATCTTGATG TGAACTCCAA CCCGGAGCAC AAGAATATCA
1561 CGGCAACCTT TATCGATAAC TACTCTCAAA TTGCCATCGA CTTTGGAAAG ACCAACTCAG
```

FIG.4A

```
1621 GCTACATCAA GCTGGGAACC AGGTATGGTG GTATCGATTG TTACGGTATC AGTGCGGATA
1681 CGGTCCCGGA AATTGTACGA CTTTATACAG GTCTTGTTGG ACGTTCAAAG TTGAAGCCCA
1741 GATATATTCT CGGGGCCCAT CAAGCCTGTA AGTCCTTCCC CTCATGAGTG ATTTATCAGA
1801 CTTGCATAAT AAACTAACCT CGTTTTCAAA GGTTATGGAT ACCAACAGGA AAGTGACTTG
1861 TATTCTGTGG TCCAGCAGTA CCGTGACTGT AAATTTCCAC TTGACGGGAT TCACGTCGAT
1921 GTCGATGTTC AGGTAAATGG CCATGGTATC ATTGAAGCTT TGAGAAATGT TCTAACTGTG
1981 TTTATAACAT TCCTAGGACG GCTTCAGAAC TTTCACCACC AACCCACACA CTTTCCCTAA
2041 CCCCAAAGAG ATGTTTACTA ACTTGAGGAA TAATGGAATC AAGTGCTCCA CCAATATCAC
2101 TCCTGTTATC AGCATTAACA ACAGAGAGGG TGGATACAGT ACCCTCCTTG AGGGAGTTGA
2161 CAAAAAATAC TTTATCATGG ACGACAGATA TACCGAGGGA ACAAGTGGGA ATGCGAAGGA
2221 TGTTCGGTAC ATGTACTACG GTGGTGGTAA TAAGGTTGAG GTCGATCCTA ATGATGTTAA
2281 TGGTCGGCCA GACTTTAAAG ACAACTAGTA AGTTGTTTAT TTGACTACGA TAGGTAACCC
2341 GTAAGCGGCA TTAACATATT TGTAGTGACT TCCCCGCGAA CTTCAACAGC AAACAATACC
2401 CCTATCATGG TGGTGTGAGC TACGGTTATG GGAACGGTAG TGTAAGTGAC GATATCTCAC
2461 CAACATAATG AAATTTATAA GGACTAACTA GACACAAAAA TTTGTAGGCA GGTTTTTACC
2521 CGGACCTCAA CAGAAAGGAG GTTCGTATCT GGTGGGGAAT GCAGTACAAG TATCTCTTCG
2581 ATATGGGACT GGAATTTGTG TGGCAAGACA TGACTACCCC AGCAATCCAC ACATCATATG
2641 GAGACATGAA AGGGTTGCCC ACCCGTCTAC TCGTCACCTC AGACTCCGTC ACCAATGCCT
2701 CTGAGAAAAA GCTCGCAATT GAAACTTGGG CTCTCTACTC CTACAATCTC CACAAAGCAA
2761 CTTGGCATGG TCTTAGTCGT CTCGAATCTC GTAAGAACAA ACGAAACTTC ATCCTCGGGC
2821 GTGGAAGTTA TGCCGGAGCC TATCGTTTTG CTGGTCTCTG GACTGGGGAT AATGCAAGTA
2881 ACTGGGAATT CTGGAAGATA TCGGTCTCTC AAGTTCTTTC TCTGGGCCTC AATGGTGTGT
2941 GCATCGCGGG GTCTGATACG GGTGGTTTTG AACCCTACCG TGATGCAAAT GGGGTCGAGG
3001 AGAAATACTG TAGCCCAGAG CTACTCATCA GGTGGTATAC TGGTTCATTC CTCTTGCCGT
3061 GGCTCAGGAA CCATTATGTC AAAAAGGACA GGAAATGGTT CCAGGTAATC TATCCTTTCT
3121 TATCTTTGAA GCATTGAAGA TACTAAGATA TAATCTAGGA ACCATACTCG TACCCCAAGC
3181 ATCTTGAAAC CCATCCAGAA CTCGCAGACC AAGCATGGCT CTATAAATCC GTTTTGGAGA
3241 TCTGTAGGTA CTATGTGGAG CTTAGATACT CCCTCATCCA ACTACTTTAC GACTGCATGT
```

*FIG.4B*

3301 TTCAAAACGT AGTCGACGGT ATGCCAATCA CCAGATCTAT G<u>GTATGTATT CTACCCTAGG</u>

3361 <u>CTTCCAGAGC AACATATGCT AACCAATTGA ACCTGGGTTT CTAG</u>CTCTTG ACCGATACTG

3421 AGGATACCAC CTTCTTCAAC GAGAGCCAAA AGTTCCTCGA CAACCAATAT ATGGCTGGTG

3481 ACGACATTCT TGTTGCACCC ATCCTCCACA GTCGCAAAGA AATTCCAGGC GAAAACAGAG

3541 ATGTCTATCT CCCTCTTTAC CACACCTGGT ACCCCTCAAA TTTGAGACCA TGGGACGATC

3601 AAGGAGTCGC TTTGGGGAAT CCTGTCGAAG GTGGTAGTGT CATCAATTAT ACTGCTAGGA

3661 TTGTTGCACC CGAGGATTAT AATCTCTTCC ACAGCGTGGT ACCAGTCTAC GTTAGAGAGG

3721 <u>GTAAGCAGTA AAATAATCTC TTCCCAGTTT CAAATACATT TAGCTAGTAG CTAACGCTAT</u>

3781 <u>GAACCTACAG</u> GTGCCATCAT CCCGCAAATC GAAGTACGCC AATGGACTGG CCAGGGGGGA

3841 GCCAACCGCA TCAAGTTCAA CATCTACCCT GGAAAGGATA AG<u>GTAAAATT CAATGATCAC</u>

3901 <u>CCTGCATCTA TTCCATCGCT GGTTTTCTTT ACCCTTACTG ACTTCATTCC TCAAAATACA</u>

3961 <u>G</u>GAGTACTGT ACCTATCTTG ATGATGGTGT TAGCCGTGAT AGTGCGCCGG AAGACCTCCC

4021 ACAGTACAAA GAGACCCACG AACAGTCGAA GGTTGAAGGC GCGGAAATCG CAAAGCAGAT

4081 TGGAAAGAAG ACGGGTTACA ACATCTCAGG AACCGACCCA GAAGCAAAGG GTTATCACCG

4141 CAAAGTTGCT GTCACACAA<u>G TAATACCGCC CTTGACTTGT ATCACTTCCT GACATCATGC</u>

4201 <u>TAATATTTCT CTGTTTACCT CAAAG</u>ACGTC AAAAGACAAG ACGCGTACTG TCACTATTGA

4261 GCCAAAACAC AATGGATACG ACCCTTCCAA AGAGGTGGGT GATTATTATA CCATCATTCT

4321 TTGGTACGCA CCAGGTTTCG ATGGCAGCAT CGTCGATGTG AGCAAGACGA CTGTGAATGT

4381 TGAGGGTGGG GTGGAGCACC AAGTTTATAA GAACTCCGAT TTACATACGG TTGTTATCGA

4441 CGTGAAGGAG GTGATCGGTA CCACAAAGAG CGTCAAGATC ACATGTACTG CCGCT*TAA*GG

4501 TCTTTTCTTG GGGCGGGAG GCGAGACCTT CGAAATGTAT ACGGGAGTGG TAACTCCGGG

4561 AAAATGGTGA TATGGGGGAT CAAGTTGGAG GGGAATCTGT TTATTTCTTT ATTTCTTTAT

4621 TTACTGGATT GGAAAATAGG GAGCACAGTT CTGACTGGAT TGGTTTGATT GTTGGCCTCT

4681 ACGGGTTCTC TTTACTTTGT CTGGAAATCC AATTTATTGT TATGCG

*FIG.4C*

```
        10         20         30         40         50         60
         |          |          |          |          |          |
   1 ATGCAGGCAA CGACAGGCGT TTTTTGTTTT ATCCGCAGAG GTGCAGCAGC AGGAAACAAA
  61 CCATACAAAC ATTCCTTGAC GCGGTTTTAG GTGCAGTTAA GGCCCGGGCG CACCAAGAAC
 121 ATTGATGTAC TTGGTCTAAA AAAGATCATA ATACCCGATT AGTGTTCATG GTTTGATTGG
 181 GTCTAAGTAC AAGTTTTACA GAGTTCAGCT TAGTTCATTG TTCGAAACTA CCAATATCAC
 241 ACCTATGCCT GCTGGCATTG ATAGCTCGGC TTGTGAAAGC TGATTACAAT CTTACATTTC
 301 TGATTTAATA TCGGACTGAT CTATATATAA GGGTCATCAT TTCCTCTCCG CCTTTTGGTT
 361 CTCTTTCATC ACCCCAGCCC AATCATCACC GTTGGCCTTT ACTTCTCTCT TCCGTTGATA
 421 TTTTCTCGAC AAAACATCTT GTCCACTGTT AGGCTAGCTC CCAGAATTAT CCCTCCAACA
 481 TGGCAGGATT ATCCGACCCT CTCAATTTCT GCAAAGCAGA GGACTACTAC GCTGCTGCCA
 541 AAGGCTGGAG TGGCCCTCAG AAGATCATTC GCTATGACCA GACCCCTCCT CAGGGTACAA
 601 AAGATCCGAA AAGCTGGCAT GCGGTAAACC TTCCTTTCGA TGACGGGACT ATGTGTGTAG
 661 TGCAATTCGT CAGACCCTGT GTTTGGAGGG TTAGATATGA CCCCAGTGTC AAGACTTCTG
 721 ATGAGTACGG CGATGAGAAT ACGTGGGTCG CCCAGTCAAT TAACTATGCC GCTAGTGATT
 781 ATGGAAAGCT TCTGCTAACC GATCAATGAG GCATGTAGGA GGACTATTGT ACAAGACTAC
 841 ATGACTACTC TGGTTGGAAA CTTGGACATT TTCAGAGGTC TTACGTGGGT TTCTACGTTG
 901 GAGGATTCGG GCGAGTACTA CACCTTCAAG GCAAGCCTCA GTGTTATATC TCGAATATAT
 961 TATATATCAC AACAAACTAA CTAGTCATAC AGTCCGAAGT CACTGCCGTG GACGAAACCG
1021 AACGGACTCG AAACAAGGTC GGCGACGGCC TCAAGATTTA CCTATGGAAA AATCCCTTTC
1081 GCATCCAGGT AGTGCGTCTC TTGACCCCCC TGGTGGACCC TTTCCCCATT CCCAACGTAG
1141 CCAATGCCAC AGCCCGTGTG GCCGACAAGG TTGTTTGGCA GACGTCCCCG AAGACGTTCA
1201 GGAAAAACTT GCATCCGCAG CATAAGATGT TGAAGGATAC AGTTCTTGAT ATTATCAAGC
1261 CGGGGCACGG AGAGTATGTG GGTTGGGGAG AGATGGGAGG CATCGAGTTT ATGAAGGAGC
1321 CAACATTCAT GAATTATTTC AGTAAGCTCT TGAAAGATTT CCTATCTCTT GACGGTCGTT
1381 TTTGCTAAGG AAACTGTAGA CTTTGACAAT ATGCAATATC AGCAGGTCTA TGCACAAGGC
1441 GCTCTTGATA GTCGTGAGCC GTTGTAAGTA ACGTCCTGTG ACATGTCATG ATTACAGTAA
1501 CTGATCGTTC AATAAGGTAT CACTCTGATC CCTTCTATCT CGACGTGAAC TCCAACCCAG
1561 AGCACAAGAA CATTACGGCA ACCTTTATCG ATAACTACTC TCAGATTGCC ATCGACTTTG
```

*FIG. 5A*

```
1621 GGAAGACCAA CTCAGGCTAC ATCAAGCTGG GTACCAGGTA TGGCGGTATC GATTGTTACG
1681 GTATCAGCGC GGATACGGTC CCGGAGATTG TGCGACTTTA TACTGGACTT GTTGGGCGTT
1741 CGAAGTTGAA GCCCAGGTAT ATTCTCGGAG CCCACCAAGC TTGTAAGCCC GCCCCCTTTA
1801 CGATGCATTT ATTAGGGGTC CACAGACTAA ACTTGTTCCA AAGGTTATGG ATACCAGCAG
1861 GAAAGTGACT TGCATGCTGT TGTTCAGCAG TACCGTGACA CCAAGTTTCC GCTTGATGGG
1921 TTGCATGTCG ATGTCGACTT TCAGgtaaat GGCCCAGGTA TCGTTGAAGC TTTGGAGAAT
1981 GCTAATTGTG CTCGTAAAAC TTTAAGGACA ATTTCAGAAC GTTACCACT AACCCGATTA
2041 CGTTCCCTAA TCCCAAAGAA ATGTTTACCA ATCTAAGGAA CAATGGAATC AAGTGTTCCA
2101 CCAACATCAC CCCTGTTATC AGTATCAGAG ATCGCCCGAA TGGGTACAGT ACCCTCAATG
2161 AGGGATATGA TAAAAAGTAC TTCATCATGG ATGACAGATA TACCGAGGGG ACAAGTGGGG
2221 ACCCGCAAAA TGTTCGATAC TCTTTTTACG GCGGTGGGAA CCCGGTTGAG GTTAACCCTA
2281 ATGATGTTTG GGCTCGGCCA GACTTTGGAG ACAATTAGTA AGTTACTCAA TAGGCTACTT
2341 GAGATATTCT GTAGGTGGCA TTAACACGAC TATAGTGACT TCCCTACGAA CTTCAACTGC
2401 AAAGACTACC CCTATCATGG TGGTGTGAGT TACGGATATG GAATGGCAC TGTAAGTGAT
2461 AATAAGTCAT AAATACAACG TAATTCATGG AGACTAATCA GTGGTAAATG AATTTTAGCC
2521 AGGTTACTAC CCTGACCTTA ACAGAGAGGA GGTTCGTATC TGGTGGGGAT TGCAGTACGA
2581 GTATCTCTTC AATATGGGAC TAGAGTTTGT ATGGCAAGAT ATGACAACCC CAGCGATCCA
2641 TTCATCATAT GGAGACATGA AAGGGTTGCC CACCCGTCTG CTCGTCACCG CCGACTCAGT
2701 TACCAATGCC TCTGAGAAAA AGCTCGCAAT TGAAAGTTGG GCTCTTTACT CCTACAACCT
2761 CCATAAAGCA ACCTTCCACG GTCTTGGTCG TCTTGAGTCT CGTAAGAACA AACGTAACTT
2821 CATCCTCGGA CGTGGTAGTT ACGCCGGTGC CTATCGTTTT GCTGGTCTCT GGACTGGAGA
2881 TAACGCAAGT ACGTGGGAAT TCTGGAAGAT TCGGTCTCC CAAGTTCTTT CTCTAGGTCT
2941 CAATGGTGTG TGTATAGCGG GGTCTGATAC GGGTGGTTTT GAGCCCGCAC GTACTGAGAT
3001 TGGGGAGGAG AAATATTGCA GTCCGGAGCT ACTCATCAGG TGGTATACTG GATCATTCCT
3061 TTTGCCATGG CTTAGAAACC ACTACGTCAA GAAGGACAGG AAATGGTTCC AGGTAATATA
3121 CTCTTTCTGG TCTCTGAGTA TCGAAGACGC TAAGACAATA TAGGAACCAT ACGCGTACCC
3181 CAAGCATCTT GAAACCCATC CAGAGCTCGC AGATCAAGCA TGGCTTTACA AATCTGTTCT
3241 AGAAATTTGC AGATACTGGG TAGAGCTAAG ATATTCCCTC ATCCAGCTCC TTTACGACTG
```

*FIG.5B*

3301 CATGTTCCAA AACGTGGTCG ATGGTATGCC ACTTGCCAGA TCTATGGTAT GCATTTTATC
3361 CGTCTCCTTT CACGATAATG CACCAGTCTA ACCGAATTTT CTTTTAGCTC TTGACCGATA
3421 CTGAGGATAC GACCTTCTTC AATGAGAGCC AAAAGTTCCT CGATAACCAA TATATGGCTG
3481 GTGACGACAT CCTTGTAGCA CCCATCCTCC ACAGCCGTAA CGAGGTTCCG GGAGAGAACA
3541 GAGATGTCTA TCTCCCTCTA TTCCACACCT GGTACCCCTC AAACTTGAGA CCGTGGGACG
3601 ATCAGGGAGT CGCTTTAGGG AATCCTGTCG AAGGTGGCAG CGTTATCAAC TACACTGCCA
3661 GGATTGTTGC CCCAGAGGAT TATAATCTCT TCCACAACGT GGTGCCGGTC TACATCAGAG
3721 AGGGTAAGCG ATGGAATAAT TTCTTGCAAG TTCCAGATAC AAGTGGTTAC TGACACCTTA
3781 AACCAGGTGC CATCATTCCG CAAATTCAGG TACGCCAGTG GATTGGCGAA GGAGGGCCTA
3841 ATCCCATCAA GTTCAATATC TACCCTGGAA AGGACAAGGT ATATTCTCCA TGACTATCGC
3901 GCATTTATTC TTTCTCTACT CGCACTAACT TCATCTGAAT ATAGGAGTAT GTGACGTACC
3961 TTGATGATGG TGTTAGCCGC GATAGTGCAC CAGATGACCT CCCGCAGTAC CGCGAGGCCT
4021 ATGAGCAAGC GAAGGTCGAA GGCAAAGACG TCCAGAAGCA ACTTGCGGTC ATTCAAGGGA
4081 ATAAGACTAA TGACTTCTCC GCCTCCGGGA TTGATAAGGA GGCAAAGGGT TATCACCGCA
4141 AAGTTTCTAT CAAACAGGTA CATGATTTCA TCTTCCTTTT TTCGCAGTCA CTATTATATC
4201 ATCCTAACAT TGCTTCTCTT ATTTAAAAGG AGTCAAAAGA CAAGACCCGT ACTGTCACCA
4261 TTGAGCCAAA ACACAACGGA TACGACCCCT CTAAGGAAGT TGGTAATTAT TATACCATCA
4321 TTCTTTGGTA CGCACCGGGC TTTGACGGCA GCATCGTCGA TGTGAGCCAG GCGACCGTGA
4381 ACATCGAGGG CGGGGTGGAA TGCGAAATTT TCAAGAACAC CGGCTTGCAT ACGGTTGTAG
4441 TCAACGTGAA AGAGGTGATC GGTACCACAA AGTCCGTCAA GATCACTTGC ACTACCGCTT
4501 AGAGCTCTTT TATGAGGGGT ATATGGGAGT GGCAGCTCAG AAATTTGGGA AGCTTCTGGG
4561 TATTCCTTTT GTTTATTTAC TTATTTATTG AATCGACCAA TACGGGTGGG ATTCTCTCTG
4621 GTTTTGTGA GGCTATGTTT TACTTGGTCT GAAAATCAAA TTCGTTCTCA

*FIG.5C*

```
MC  - MAGFSDPLNFCKAEDYYSVALDWKGPQKIIGVDTTPPKSTKFPKNWHGVN -50
      ::: :::::::::::::.  :   :  :::::::    : :::   :: ::   :: ::
MV  - MAGLSDPLNFCKAEDYYAAAKGWSGPQKIIRYDQTPPQGTKDPKSWHAVN -50

MC  - LRFDDGTLGVVQFIRPCVWRVRYDPGFKTSDEYGDENTRTIVQDYMSTLS -100
      : ::::::.  ::::.:::::::::::  :::::::::::::::::::.:
MV  - LPFDDGTMCVVQFVRPCVWRVRYDPSVKTSDEYGDENTRTIVQDYMTTLV -100

MC  - NKLDTYRGLTWETKCEDSGDFFTFSSKVTAVEKSERTRNKVGDGLRIHLW -150
      :: .:::::  .   ::::::..:: : :::: .:::::::::::  :: ::
MV  - GNLDIFRGLTWVSTLEDSGEYYTFKSEVTAVDETERTRNKVGDGLKIYLW -150

MC  - KSPFRIQVVRTLTPLKDPYPIPNVAAAEARVSDKVVWQTSPKTFRKNLHP -200
      : :::::::: ::::  ::.::::::::::.:::::::::::::::::::
MV  - KNPFRIQVVRLLTPLVDPFPIPNVANATARVADKVVWQTSPKTFRKNLHP -200

MC  - QHKMLKDTVLDIVKPGHGEYVGWGEMGGIQFMKEPTFMNYFNFDNMQYQQ -250
      :::::::::::::.::::::::::::::::.:::::::::::::::::::
MV  - QHKMLKDTVLDIIKPGHGEYVGWGEMGGIEFMKEPTFMNYFNFDNMQYQQ -250

MC  - VYAQGALDSREPLYHSDPFYLDVNSNPEHKNITATFIDNYSQIAIDFGKT -300
      ::::::::::::::::::::::::::::::::::::::::::::::::::
MV  - VYAQGALDSREPLYHSDPFYLDVNSNPEHKNITATFIDNYSQIAIDFGKT -300

MC  - NSGYIKLGTRYGGIDCYGISADTVPEIVRLYTGLVGRSKLKPRYILGAHQ -350
      ::::::::::::::::::::::::::::::::::::::::::::::::::
MV  - NSGYIKLGTRYGGIDCYGISADTVPEIVRLYTGLVGRSKLKPRYILGAHQ -350

MC  - ACYGYQQESDLYSVVQQYRDCKFPLDGIHVDVDVQDGFRTFTTNPHTFPN -400
      :::::::::::: ..::::::: ::::::.:::: ::: ::::::: :::
MV  - ACYGYQQESDLHAVVQQYRDTKFPLDGLHVDVDFQDNFRTFTTNPITFPN -400

MC  - PKEMFTNLRNNGIKCSTNITPVISINNREGGYSTLLEGVDKKYFIMDDRY -450
      :::::::::::::::::::::::::: ::  :::::.: ::::::::::::
MV  - PKEMFTNLRNNGIKCSTNITPVISIRDRPNGYSTLNEGYDKKYFIMDDRY -450

MC  - TEGTSGNAKDVRYMYYGGGNKVEVDPNDVNGRPDFKDNYDFPANFNSKQY -500
      ::::::::  :::  ::::::: ::::::::.  :::: ::::.:: : :
MV  - TEGTSGDPQNVRYSFYGGGNPVEVNPNDVWARPDFGDNYDFPTNFNCKDY -500

MC  - PYHGGVSYGYGNGSAGFYPDLNRKEVRIWWGMQYKYLFDMGLEFVWQDMT -550
      ::::::::::::: . ::::::::: ::::: ::::::::::::::::::
MV  - PYHGGVSYGYGNGTPGYYPDLNREEVRIWWGLQYEYLFNMGLEFVWQDMT -550

MC  - TPAIHTSYGDMKGLPTRLLVTSDSVTNASEKKLAIETWALYSYNLHKATW -600
      :::::.::::::::::::::::::::::::::::::::::::::::::::
MV  - TPAIHSSYGDMKGLPTRLLVTADSVTNASEKKLAIESWALYSYNLHKATF -600

MC  - HGLSRLESRKNKRNFILGRGSYAGAYRFAGLWTGDNASNWEFWKISVSQV -650
      ::: :::::::::::::::::::::::::::::::::  ::::::::::::
MV  - HGLGRLESRKNKRNFILGRGSYAGAYRFAGLWTGDNASTWEFWKISVSQV -650

MC  - LSLGLNGVCIAGSDTGGFEPYRDANGVEEKYCSPELLIRWYTGSFLLPWL -700
      :::::::::::::::::::::   :  :::::::::::::::::::::::
MV  - LSLGLNGVCIAGSDTGGFEPAR-TEIGEEKYCSPELLIRWYTGSFLLPWL -699
```

*FIG. 6A*

```
MC    -  RNHYVKKDRKWFQEPYSYPKHLETHPELADQAWLYKSVLEICRYYVELRY  -750
         ::::::::::::::::::::..:::::::::::::::::::::::.::::
MV    -  RNHYVKKDRKWFQEPYAYPKHLETHPELADQAWLYKSVLEICRYWVELRY  -749

MC    -  SLIQLLYDCMFQNVVDGMPITRSMLLTDTEDTTFFNESQKFLDNQYMAGD  -800
         ::::::::::::::::::::::..::::::::::::::::::::::::::
MV    -  SLIQLLYDCMFQNVVDGMPLARSMLLTDTEDTTFFNESQKFLDNQYMAGD  -799

MC    -  DILVAPILHSRKEIPGENRDVYLPLYHTWYPSNLRPWDDQGVALGNPVEG  -850
         ::::::::::: :.::::::::::::.:::::::::::::::::::::::
MV    -  DILVAPILHSRNEVPGENRDVYLPLFHTWYPSNLRPWDDQGVALGNPVEG  -849

MC    -  GSVINYTARIVAPEDYNLFHSVVPVYVREGAIIPQIEVRQWTGQGGANRI  -900
         ::::::::::::::::::.:::::.::::::::.:.:::::  :: : :
MV    -  GSVINYTARIVAPEDYNLFHNVVPVYIREGAIIPQIQVRQWIGEGGPNPI  -899

MC    -  KFNIYPGKDKEYCTYLDDGVSRDSAPEDLPQYKETHEQSKVEGAEIAKQI  -950
         :::::::::::: :::::::::::::: ::::::.: :....::.:.:.
MV    -  KFNIYPGKDKEYVTYLDDGVSRDSAPDDLPQYREAYEQAKVEGKDVQKQL  -949

MC    -  G-----KKTGYNISGTDPEAKGYHRKVAVTQTSKDKTRTVTIEPKHNGYD  -995
         :     .  :: : ::::::.. : :::::::::::::::::::::::
MV    -  AVIQGNKTNDFSASGIDKEAKGYHRKVSIKQESKDKTRTVTIEPKHNGYD  -999

MC    -  PSKEVGDYYTIILWYAPGFDGSIVDVSKTTVNVEGGVEHQVYKNSDLHTV  -1045
         ::::::.:::::::::::::::::::. .:::.::::: .::.:. :::
MV    -  PSKEVGNYYTIILWYAPGFDGSIVDVSQATVNIEGGVECEIFKNTGLHTV  -1049

MC    -  VIDVKEVIGTTKSVKITCTAA  -1066
         :.::::::::::::::::::.:
MV    -  VVNVKEVIGTTKSVKITCTTA  -1070
```

```
MAGFSDPLNF CKAEDYYSVA LDWKGPQKII GVDTTPPKST KFPKNWHGVN LRFDDGTLGV VQFIRPCVWR
VRYDPGFKTS DEYGDENTRT IVQDYMSTLS NKLDTYRGLT WETKCEDSGD FFTFSSKVTA VEKSERTRNK
VGDGLRIHLW KSPFRIQVVR TLTPLKDPYP IPNVAAAEAR VSDKVVWQTS PKTFRKNLHP QHKMLKDTVL
DIVKPGHGEY VGWGEMGGIQ FMKEPTFMNY FNFDNMQYQQ VYAQGALDSR EPLYHSDPFY LDVNSNPEHK
NITATFIDNY SQIAIDFGKT NSGYIKLGTR YGGIDCYGIS ADTVPEIVRL YTGLVGRSKL KPRYILGAHQ
ACYGYQQESD LYSVVQQYRD CKFPLDGIHV DVDVQDGFRT FTTNPHTFPN PKEMFTNLRN NGIKCSTNIT
PVISINNREG GYSTLLEGVD KKYFIMDDRY TEGTSGNAKD VRYMYYGGGN KVEVDPNDVN GRPDFKDNYD
FPANFNSKQY PYHGGVSYGY GNGSAGFYPD LNRKEVRIWW GMQYKYLFDM GLEFVWQDMT TPAIHTSYGD
MKGLPTRLLV TSDSVTNASE KKLAIETWAL YSYNLHKATW HGLSRLESRK NKRNFILGRG SYAGAYRFAG
LWTGDNASNW EFWKISVSQV LSLGLNGVCI AGSDTGGFEP YRDANGVEEK YCSPELLIRW YTGSFLLPWL
RNHYVKKDRK WFQEPYSYPK HLETHPELAD QAWLYKSVLE ICRYYVELRY SLIQLLYDCM FQNVVDGMPI
TRSMLLTDTE DTTFFNESQK FLDNQYMAGD DILVAPILHS RKEIPGENRD VYLPLYHTWY PSNLRPWDDQ
GVALGNPVEG GSVINYTARI VAPEDYNLFH SVVPVYVREG AIIPQIEVRQ WTGQGGANRI KFNIYPGKDK
EYCTYLDDGV SRDSAPEDLP QYKETHEQSK VEGAEIAKQI GKKTGYNISG TDPEAKGYHR KVAVTQTSKD
KTRTVTIEPK HNGYDPSKEV GDYYTIILWY APGFDGSIVD VSKTTVNVEG GVEHQVYKNS DLHTVVIDVK
EVIGTTKSVK ITCTAA
```

FIGURE 8

```
MAGLSDPLNF RKAEDYYAAA KGWSGPQKII RYDQTPPQGT KDPKSWHAVN LPFDDGTMCV VQFVRPCVWR
VRYDPSVKTS DEYGDENTRT IVQDYMTTLV GNLDIFRGLT WVSTLEDSGE YYTFKSEVTA VDETERTRNK
VGDGLKIYLW KNPFRIQVVR LLTPLVDPFP IPNVANATAR VADKVVWQTS PKTFRKNLHP QHKMLKDTVL
DIIKPGHGEY VGWGEMGGIE FMKEPTFMNY FNFDNMQYQQ VYAQGALDSR EPLYHSDPFY LDVNSNPEHK
NITATFIDNY SQIAIDFGKT NSGYIKLGTR YGGIDCYGIS ADTVPEIVRL YTGLVGRSKL KPRYILGAHQ
ACYGYQQESD LHAVVQQYRD TKFPLDGLHV DVDFQDNFRT FTTNPITFPN PKEMFTNLRN NGIKCSTNIT
PVISIRDRPN GYSTLNEGYD KKYFIMDDRY TEGTSGDPQN VRYSFYGGGN PVEVNPNDVW ARPDFGDNYD
FPTNFNCKDY PYHGGVSYGY GNGTPGYYPD LNREEVRIWW GLQYEYLFNM GLEFVWQDMT TPAIHSSYGD
MKGLPTRLLV TADSVTNASE KKLAIESWAL YSYNLHKATF HGLGRLESRK NKRNFILGRG SYAGAYRFAG
LWTGDNASTW EFWKISVSQV LSLGLNGVCI AGSDTGGFEP ARTEIGEEKY CSPELLIRWY TGSFLLPWLR
NHYVKKDRKW FQEPYAYPKH LETHPELADQ AWLYKSVLEI CRYWVELRYS LIQLLYDCMF QNVVDGMPLA
RSMLLTDTED TTFFNESQKF LDNQYMAGDD ILVAPILHSR NEVPGENRDV YLPLFHTWYP SNLRPWDDQG
VALGNPVEGG SVINYTARIV APEDYNLFHN VVPVYIREGA IIPQIQVRQW IGEGGPNPIK FNIYPGKDKE
YVTYLDDGVS RDSAPDDLPQ YREAYEQAKV EGKDVQKQLA VIQGNKTNDF SASGIDKEAK GYHRKVSIKQ
ESKDKTRTVT IEPKHNGYDP SKEVGNYYTI ILWYAPGFDG SIVDVSQATV NIEGGVECEI FKNTGLHTVV
VNVKEVIGTT KSVKITCTTA
```

α-1,4-GLUCAN LYASE FROM A FUNGUS, ITS PURIFICATION GENE CLONING AND EXPRESSION IN MICROORGANISMS

The present invention relates to an enzyme, in particular α-1,4-glucan lyase ("GL"). The present invention also relates to a method of extracting same.

FR-A-2617502 and Baute et al in Phytochemistry [1988] vol. 27 No. 11 pp 3401–3403 report on the production of 1,5-D-anhydrofructose ("AF") in *Morchella vulganis* by an apparent enzymatic reaction. The yield of production of AF is quite low. Despite a reference to a possible enzymatic reaction, neither of these two documents presents any amino acid sequence data for any enzyme let alone any nucleotide sequence information. These documents say that AF can be a precursor for the preparation of the antibiotic pyrone microthecin.

Yu et al in Biochimica et Biophysica Acta [1993] vol 1156 pp 313–320 report on the preparation of GL from red seaweed and its use to degrade α-1,4-glucan to produce AF. The yield of production of AF is quite low. Despite a reference to the enzyme GL this document does not present any amino acid sequence data for that enzyme let alone any nucleotide sequence information coding for the same. This document also suggests that the source of GL is just algal.

According to the present invention there is provided a method of preparing the enzyme α-1,4-glucan lyase comprising isolating the enzyme from a culture of a fungus wherein the culture is substantially free of any other organism.

Preferably the enzyme is isolated and/or further purified using a gel that is not degraded by the enzyme.

Preferably the gel is based on dextrin or derivatives thereof, preferably a cyclodextrin, more preferably beta-cyclodextrin.

According to the present invention there is also provided a GL enzyme prepared by the method of the present invention.

Preferably the fungus is *Morchella costata* or *Morchella vulgaris*.

Preferably the enzyme comprises the amino acid sequence SEQ. ID. No. 1 or SEQ. I.D. No. 2, or any variant thereof.

The term "any variant thereof" means any substitution of, variation of, modification of, replacement of, deletion of or addition of an amino acid from or to the sequence providing the resultant enzyme has lyase activity.

According to the present invention there is also provided a nucleotide sequence coding for the enzyme α-1,4-glucan lyase, preferably wherein the sequence is not in its natural enviroment (i.e. it does not form part of the natural genome of a cellular organism expressing the enzyme).

Preferably the nucleotide sequence is a DNA sequence.

Preferably the DNA sequence comprises a sequence that is the same as, or is complementary to, or has substantial homology with, or contains any suitable codon substitution (s) for any of those of, SEQ. ID. No. 3 or SEQ. ID. No. 4.

The expression "substantial homology" covers homology with respect to structure and/or nucleotide components and/or biological activity.

The expression "contains any suitable codon substitutions" covers any codon replacement or substitution with another codon coding for the same amino acid or any addition or removal thereof providing the resultant enzyme has lyase activity.

In other words, the present invention also covers a modified DNA sequence in which at least one nucleotide has been deleted, substituted or modified or in which at least one additional nucleotide has been inserted so as to encode a polypeptide having the activity of a glucan lyase, preferably an enzyme having an increased lyase activity.

According to the present invention there is also provided a method of preparing the enzyme α-1,4-glucan lyase comprising expressing the nucleotide sequence of the present invention.

According to the present invention there is also provided the use of beta-cyclodextrin to purify an enzyme, preferably GL.

According to the present invention there is also provided a nucleotide sequence wherein the DNA sequence is made up of at least a sequence that is the same as, or is complementary to, or has substantial homology with, or contains any suitable codon substitutions for any of those of, SEQ. ID. No. 3 or SEQ. ID. No. 4, preferably wherein the sequence is in isolated form.

The present invention therefore relates to the isolation of the enzyme α-1,4-glucan lyase from a fungus. For example, the fungus can be any one of *Discina perlata, Discina parma, Gyromitra gigas, Gyromitra infula, Mitrophora hybrida, Morchella conica, Morchella costata, Morchella elata, Morchella hortensis, Morchella rotunda, Morchella vulgaris, Peziza badia, Sarcosphaera eximia, Disciotis venosa, Gyromitra esculenta, Helvella crispa, Helvella lacunosa, Leptopodia elastica, Verpa digitaliformis*, and other forms of Morchella. Preferably the fungus is *Morchella costata* or *Morchella vulgaris*.

The initial enzyme purification can be performed by the method as described by Yu et al (ibid).

However, preferably, the initial enzyme purification includes an optimized procedure in which a solid support is used that does not decompose under the purification step. This gel support further has the advantage that it is compatible with standard laboratory protein purification equipment.

The details of this optimized purification strategy are given later on. The purification is terminated by known standard techniques for protein purification.

The purity of the enzyme can be readily established using complementary electrophoretic techniques.

The purified lyase GL has been characterized according to pI, temperature- and pH-optima.

In this regard the fungal lyase shows a pI around 5.4 as determined by isoelectric focusing on gels with pH gradient of 3 to 9. The molecular weight determined by SDS-PAGE on 8–25% gradient gels was 110 kDa. The enzyme exhibits a pH optimum in the range pH 5–7. The temperature optimum was found to lay between 30–45° C.

| GL sources | Optimal pH | Optimal pH range | Optimal temperature |
| --- | --- | --- | --- |
| M. costata | 6.5 | 5.5–7.5 | 37 C; 40 C[a] |
| M. vulgaris | 6.4 | 5.9–7.6 | 43 C; 48 C[a] |

Parameters determined using glycogen as substrate; other parameters determined using amylopectin as substrate.

In a preferred embodiment the α-1,4-glucan lyase is purified from the fungus *Morchella costata* by affinity chromatography on β-cyclodextrin Sepharose, ion exchange on Mono Q HR 5/5 and gel filtration on Superose 12 columns.

PAS staining indicates that the fungal lyase was not glycosylated. In the cell-free fungus extract, only one form of α-1,4-glucan lyase was detected by activity gel staining on electrophoresis gels.

The enzyme should preferably be secreted to ease its purification. To do so the DNA encoding the mature enzyme is fused to a signal sequence, a promoter and a terminator from the chosen host.

For expression in *Aspergillus niger* the gpdA (from the Glyceraldehyde-3-phosphate dehydrogenase gene of *Aspergillus nidulans*) promoter and signal sequence is fused to the 5' end of the DNA encoding the mature lyase—such as SEQ I.D. No. 3 or SEQ. I.D. No. 4. The terminator sequence from the *A. niger* trpC gene is placed 3' to the gene (Punt, P. J. et al (1991): J. Biotech. 17, 19–34). This construction is inserted into a vector containing a replication origin and selection origin for *E. coli* and a selection marker for *A. niger*. Examples of selection markers for *A. niger* are the amdS gene, the argB gene, the pyrG gene, the hygB gene, the BmlR gene which all have been used for selection of transformants. This plasmid can be transformed into *A. niger* and the mature lyase can be recovered from the culture medium of the transformants.

The construction can be transformed into a protease deficient strain to reduce the proteolytic degradation of the lyase in the culture medium (Archer D. B. et al (1992): Biotechnol. Lett. 14, 357–362).

The amino acid composition can be established according to the method of Barholt and Jensen (Anal Biochem [1989] vol 177 pp 318–322). The sample for the amino acid analysis of the purified enzyme can contain 69 ug/ml protein.

The amino acid sequence of the GL enzymes according to the present invention are shown in SEQ. I.D. No. 1 and SEQ. I.D. No. 2.

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on Oct. 3, 1994:

*E. Coli* containing plasmid pMC (NCIMB 40687)—[ref. DH5alpha-pMC];

*E. Coli* containing plasmid pMV1 (NCIMB 40688)—[ref. DH5alpha-pMV1]; and

*E. Coli* containing plasmid pMV2 (NCIMB 40689)—[ref. DH5alpha-pMV2].

Plasmid pMC is a pBluescript II KS containing a 4.1 kb fragment isolated from a genomic library constructed from *Morchella costata*. The fragment contains a gene coding for α-1,4-glucan lyase.

Plasmid pMV1 is a pBluescript II KS containing a 2.45 kb fragment isolated from a genomic library constructed from *Morchella vulgaris*. The fragment contains the 5' end of a gene coding for α-1,4-glucan lyase.

Plasmid MV2 is a pPUC19 containing a 3.1 kb fragment isolated from a genomic library constructed from Morchella vulgaris. The fragment contains the 3' end of a gene coding for α-1,4-glucan lyase.

In the following discussion, MC represents *Morchella costata* and MV represents *Morchella vulgaris*.

As mentioned, the GL coding sequence from *Morchella vulgaris* was contained in two plasmids. With reference to FIG. 5 (discussed later) pMV1 contains the nucleotides from position 454 to position 2902; and pMV2 contains the nucleotides downstream from (and including) position 2897. With reference to FIGS. 2 and 3 (discussed later), to ligate the coding sequences one can digest pMV2 with restriction enzymes EcoRI and BamHI and then insert the relevant fragment into pMV1 digested with restriction enzymes EcoRI and BamHI.

Thus highly preferred embodiments of the present invention include a GL enzyme obtainable from the expression of the GL coding sequences present in plasmids that are the subject of either deposit NCIMB 40687 or deposit NCIMB 40688 and deposit NCIMB 40689.

The present invention will now be described only by way of example.

BRIEF DESCRIPTION OF THE DRAWINGS

In the following Examples reference is made to the accompanying figures in which:

FIG. 4 shows the GL coding sequence and part of the 5' and 3' non-translated regions for genomic DNA obtained from *Morchella costata*;

FIG. 5 shows the GL coding sequence and part of the 5' and 3' non-translated regions for genomic DNA obtained from *Morchella vulganis*;

FIG. 6 shows a comparison of the GL coding sequences and non-translated regions from *Morchella costata* and *Morchella vulgaris*;

FIG. 7 shows the amino acid sequence represented as SEQ. I.D. No. 1 showing positions of the peptide fragments that were sequenced; and FIG. 8 shows the amino acid sequence represented as SEQ. I.D. No. 2 showing positions of the peptide fragments that were sequenced.

Figure 1:
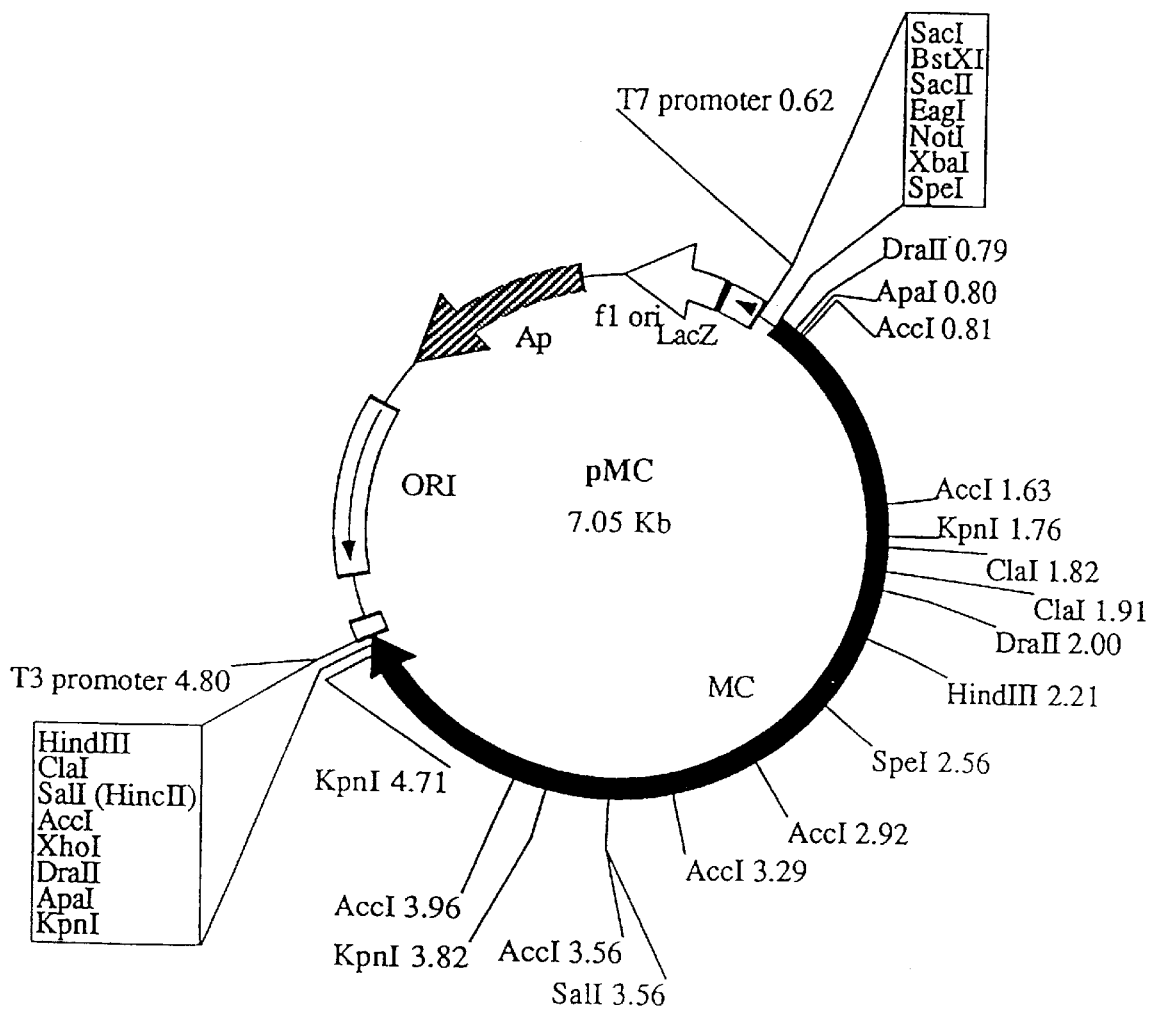
FIG. 1 shows a plasmid map of pMC.
Figure 2:
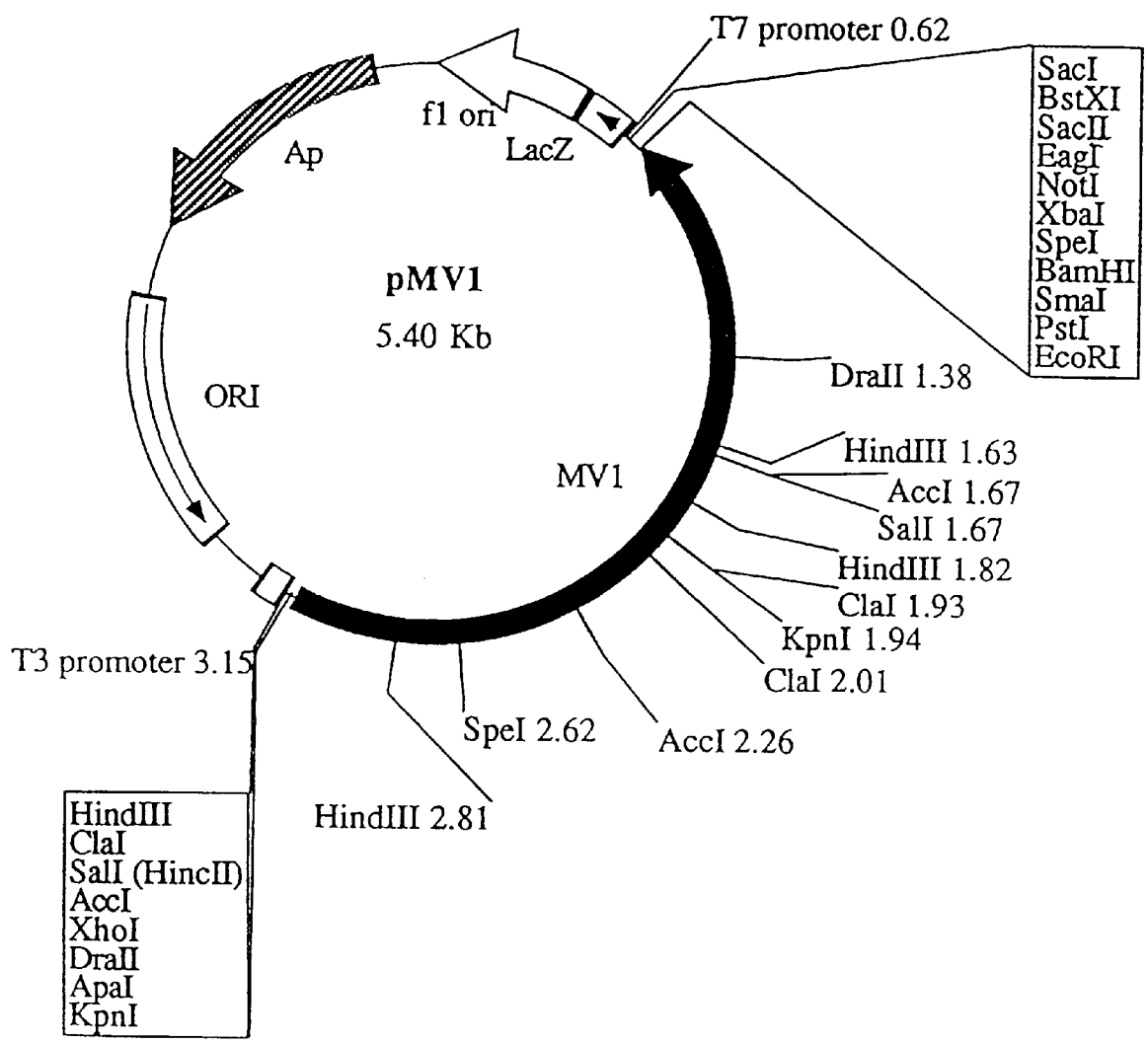
FIG. 2 shows a plasmid map of pMV1.
Figure 3:
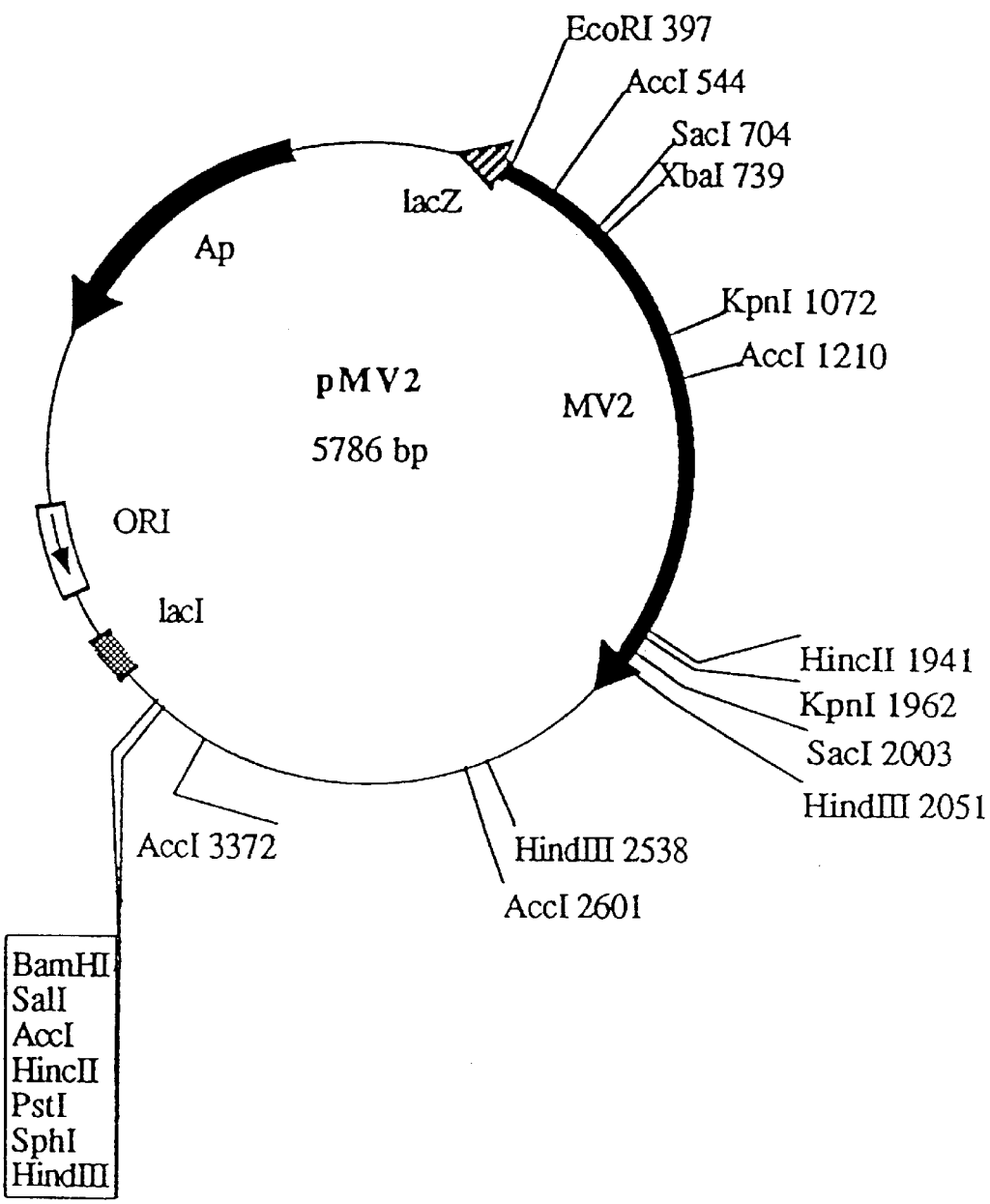
FIG. 3 shows a plasmid map of pMV2.

In more detail, in FIG. 4, the total number of bases is 4726—and the DNA sequence composition is: 1336 A; 1070 C; 1051 G; 1269 T. The ATG start codon is shown in bold. The introns are underlined. The stop codon is shown in italics.

In FIG. 5, the total number of bases is 4670—and the DNA sequence composition is: 1253 A; 1072 C; 1080 G; 1265 T. The ATG start codon is shown in bold. The introns are underlined. The stop codon is shown in italics.

In FIG. 6, the two aligned sequences are those obtained from MC (total number of residues: 1066) and MV (total number of residues: 1070). The comparison matrix used was a structure-genetic matrix (Open gap cost: 10; Unit gap cost: 2). In this, Figure, the character to show that two aligned residues are identical is ':'. The character to show that two aligned residues are similar is '.'. The amino acids said to be 'similar' are: A,S,T; D,E; N,Q; R,K; I,L,M,V; F,Y,W. Overall there is: Identity: 920 (86.30%); Similarity: 51 (4.78%). The number of gaps inserted in MC is 1 and the number of gaps inserted in MV is 1.

In the attached sequence listings: SEQ. I.D.No. 1 is the amino-acid sequence for GL obtained from *Morchella costata*; SEQ. I.D.No. 2 is the amino-acid sequence for GL obtained from *Morchella vulgaris*; SEQ. I.D.No. 3 is the nucleotide coding sequence for GL obtained from *Morchella costata*; and SEQ. I.D.No. 4 is the nucleotide coding sequence for GL obtained from *Morchella vulganis*.

In SEQ. I.D. No. 1 the total number of residues is 1066. The GL enzyme has an amino acid composition of:

| 46 Ala | 13 Cys | 25 His | 18 Met | 73 Thr |
|--------|--------|--------|--------|--------|
| 50 Arg | 37 Gln | 54 Ile | 43 Phe | 23 Trp |
| 56 Asn | 55 Glu | 70 Leu | 56 Pro | 71 Tyr |
| 75 Asp | 89 Gly | 71 Lys | 63 Ser | 78 Val |

In SEQ.I.D. No. 2 the total number of residues is 1070. The GL enzyme has an amino acid composition of:

| 51 Ala | 13 Cys | 22 His | 17 Met | 71 Thr |
| --- | --- | --- | --- | --- |
| 50 Arg | 40 Gln | 57 Ile | 45 Phe | 24 Trp |
| 62 Asn | 58 Glu | 74 Leu | 62 Pro | 69 Tyr |
| 74 Asp | 87 Gly | 61 Lys | 55 Ser | 78 Val |

1. ENZYME PURIFICATION AND CHARACTERIZATION OF THE α-1,4-GLUCAN LYASE FROM THE FUNGUS MORCHELLA COSTATA

1.1 Materials and Methods

The fungus *Morchella costata* was obtained from American Type Culture Collection (ATCC). The fungus was grown at 25° C. on a shaker using the culture medium recommended by ATCC. The mycelia were harvested by filtration and washed with 0.9% NaCl.

The fungal cells were broken by homogenization followed by sonication on ice for 6×3 min in 50 mM citrate-NaOH pH 6.2 (Buffer A). Cell debris were removed by centrifugation at 25,000×g for 40 min. The supernatant obtained at this procedure was regarded as cell-free extract and was used for activity staining and Western blotting after separation on 8–25% gradient gels.

1.2 Separation by β-cyclodextrin Sepharose gel

The cell-free extract was applied directly to a β-cyclodextrin Sepharose gel 4B clolumn (2.6×18 cm) pre equilibrated with Buffer A. The column was washed with 3 volumes of Buffer A and 2 volumes of Buffer A containing 1M NaCl. α-1,4-glucan lyase was eluted with 2% dextrins in Buffer A. Active fractions were pooled and the buffer changed to 20 mM Bis-tris propane-HCl (pH 7.0, Buffer B).

Active fractions were applied onto a Mono Q HR 5/5 column pre-equilibrated with Buffer B. The fungal lyase was eluted with Buffer B in a linear gradient of 0.3M NaCl.

The lyase preparation obtained after β-cyclodextrin Sepharose chromatography was alternatively concentrated to 150 µl and applied on a Superose 12 column operated under FPLC conditions.

1.3 Assay for α-1,4-glucan lyase activity and conditions for determination of substrate specificity, pH and temperature optimum The reaction mixture for the assay of the α-1,4-glucan lyase activity contained 10 mg ml$^{-1}$ amylopectin and 25 mM Mes-NaOH (pH 6.0).

The reaction was carried out at 30° C. for 30 min and stopped by the addition of 3,5-dinitrosalicylic acid reagent. Optical density at 550 nm was measured after standing at room temperature for 10 min. 10 mM EDTA was added to the assay mixture when cell-free extracts were used.

The substrate amylopectin in the assay mixture may be replaced with other substrates and the reaction temperature may vary as specified in the text.

In the pH optimum investigations, the reaction mixture contained amylopection or maltotetraose 10 mg ml$^{-1}$ in a 40 mM buffer. The buffers used were glycine-NaOH (pH 2.0–3.5), HoAc-NaoAc (pH 3.5–5.5), Mes-NaOH (pH 5.5–6.7), Mops-NaOH (6.0–8.0) and bicine-NaOH (7.6–9.0). The reactions were carried out at 30° C. for 30 min. The reaction conditions in the temperature optimum investigations was the same as above except that the buffer Mops-NaOH (pH 6.0) was used in all experiments. The reaction temperature was varied as indicated in the text.

SDS-PAGE, Native-PAGE and isoelectrofocusing were performed on PhastSystem (Pharmacia, Sweden) using 8–25% gradient gels and gels with a pH gradient of 3–9, respectively. Following electrophoresis, the gels were stained by silver staining according to the procedures recommended by the manufacturer (Pharmacia). The glycoproteins were stained by PAS adapted to the PhastSystem. For activity staining, the electrophoresis was performed under native conditions at 6° C.

Following the electrophoresis, the gel was incubated in the presence of 1% soluble starch at 30° C. overnight. Activity band of the fungal lyase was revealed by staining with $I_2$/KI solution.

1.4 Results

1.4.1 Purification, molecular mass and isoelectric point of the α-1,4-glucan lyase The fungal lyase was found to adsorb on columns packed with β-cyclodextrin Sepharose, starches and Red Sepharose. Columns packed with β-cyclodextrin Sepharose 4B gel and starches were used for purification purposes.

The lyase preparation obtained by this step contained only minor contaminating proteins having a molecular mass higher than the fungal lyase. The impurity was either removed by ion exchange chromatography on Mono Q HR 5/5 or more efficiently by gel filtration on Superose 12.

The purified enzyme appeared colourless and showed no absorbance in the visible light region. The molecular mass was determined to 110 kDa as estimated on SDS-PAGE.

The purified fungal lyase showed a isoelectric point of pI 5.4 determined by isoelectric focusing on gels with a pH gradient of 3 to 9. In the native electrophoresis gels, the enzyme appeared as one single band. This band showed starch-degrading activity as detected by activity staining. Depending the age of the culture from which the enzyme is extracted, the enzyme on the native and isoelectric focusing gels showed either as a sharp band or a more diffused band with the same migration rate and pI.

1.4.2 The pH and temperature optimum of the fungal lyase catalayzed reaction The pH optimum pH range for the fungal lyase catalyzed reaction was found to be between pH 5 and pH 7.

1.4.3 Substrate specificity

The purified fungal lyase degraded maltosaccharides from maltose to maltoheptaose. However, the degradation rates varied. The highest activity achieved was with maltotetraose (activity as 100%), followed by maltohexaose (97%), maltoheptaose (76%), maltotriose (56%) and the lowest activity was observed with maltose (2%).

Amylopectin, amylose and glycogen were also degraded by the fungal lyase (% will be determined). The fungal lyase was an exo-lyase, not a endolyase as it degraded p-nitrophenyl α-D-maltoheptaose but failed to degrade reducing end blocked p-nitrophenyl (α-D-maltoheptaose.

1.5 Morchella Vulgaris

The protocols for the enzyme purification and charaterisation of alpha 1,4-glucal lyase obtained from Morchella Vulgaris were the same as those above for Morchella Costata (with similar results—see results mentioned above).

2. AMINO ACID SEQUENCING OF THE α-1,4-GLUCAN LYASE FROM FUNGUS

2.1 Amino acid sequencing of the lyases

The lyases were digested with either endoproteinase Arg-C from *Clostridium histolyticum* or endoproteinase Lys-C from *Lysobacter enzymogenes*, both sequencing grade purchased from Boehringer Mannheim, Germany. For digestion with endoproteinase Arg-C, freezedried lyase (0.1 mg) was dissolved in 50 µl 10M urea, 50 mM methylamine, 0.1M Tris-HCl, pH 7.6. After overlay with $N_2$ and addition of 10 µl of 50 mM DTT and 5 mM EDTA the protein was denatured and reduced for 10 min at 50° C. under $N_2$. Subsequently, 1 µg of endoproteinase Arg-C in 10 µl of 50 mM Tris-HCl, pH 8.0 was added, $N_2$ was overlayed and the digestion was carried out for 6 h at 37° C.

For subsequent cysteine derivatization, 12.5 μl 100 mM iodoacetamide was added and the solution was incubated for 15 min at RT in the dark under $N_2$.

For digestion with endoproteinase Lys-C, freeze dried lyase (0.1 mg) was dissolved in 50 μl of 8M urea, 0.4M $NH_4HCO_3$, pH 8.4. After overlay with $N_2$ and addition of 5 μl of 45 mM DTT, the protein was denatured and reduced for 15 min at 50° C. under $N_2$. After cooling to RT, 5 μl of 100 mM iodoacetamide was added for the cysteines to be derivatized for 15 min at RT in the dark under $N_2$. Subsequently, 90 μl of water and 5 μg of endoproteinase Lys-C in 50 μl of 50 mM tricine and 10 mM EDTA, pH 8.0, was added and the digestion was carried out for 24 h at 37° C. under $N_2$.

The resulting peptides were separated by reversed phase HPLC on a VYDAC C18 column (0.46×15 cm; 10 μm; The Separations Group; California) using solvent A: 0.1% TFA in water and solvent B: 0.1% TFA in acetonifile. Selected peptides were rechromatographed on a Develosil C18 column (0.46×10 cm; 3 μm; Dr. Ole Schou, Novo Nordisk, Denmark) using the same solvent system prior to sequencing on an Applied Biosystems 476A sequencer using pulsed-liquid fast cycles.

The amino acid sequence information from the enzyme derived from the fungus *Morchella costata* is shown FIG. 7.

The amino acid sequence information from the enzyme derived from the fungus *Morchella vulgaris* is shown FIG. 8.

3. DNA SEQUENCING OF GENES CODING FOR THE α-1,4-GLUCAN LYASE FROM FUNGUS

3.1 METHODS FOR MOLECULAR BIOLOGY

DNA was isolated as described by Dellaporte et al (1983—Plant Mol Biol Rep vol 1 pp 19–21).

3.2 PCR

The preparation of the relevant DNA molecule was done by use of the Gene Amp DNA Amplification Kit (Perkin Elmer Cetus, USA) and in accordance with the manufactures instructions except that the Taq polymerase was added later (see PCR cycles) and the temperature cycling was changed to the following:

| PCR cycles: | | |
| --- | --- | --- |
| no of cycles | C | time (min.) |
| 1 | 98 | 5 |
|  | 60 | 5 |
| addition of Taq polymerase and oil | | |
| 35 | 94 | 1 |
|  | 47 | 2 |
|  | 72 | 3 |
| 1 | 72 | 20 |

3.3 CLONING OF PCR FRAGMENTS

PCR fragments were cloned into pT7Blue (from Novagen) following the instructions of the supplier.

3.4 DNA SEQUENCING

Double stranded DNA was sequenced essentially according to the dideoxy method of Sanger et al. (1979) using the Auto Read Sequencing Kit (Pharmacia) and the Pharmacia LKB A.L.F.DNA sequencer. (Ref: Sanger, F., Nicklen, S. and Coulson, A. R. (1979). DNA sequencing with chain-determinating inhibitors. Proc. Natl. Acad. Sci. USA 74: 5463–5467.)

3.5 SCREENING OF THE LIBRARIES

Screening of the Lambda Zap libraries obtained from Stratagene, was performed in accordance with the manufacturer's instructions except that the prehybridization and hybridization was performed in 2×SSC, 0.1% SDS, 10×Denhardt's and 100 μg/ml denatured salmon sperm DNA.

To the hybridization solution a 32P-labeled denatured probe was added. Hybridization was performed over night at 55° C. The filters were washed twice in 2×SSC, 0.1% SDS and twice in 1×SSC, 0.1% SDS.

3.6 PROBE

The cloned PCR fragments were isolated from the pT7blue vector by digestion with appropriate restriction enzymes. The fragments were seperated from the vector by agarose gel electrophoresis and the fragments were purified from the agarose by Agarase (Boehringer Mannheim). As the fragments were only 90–240 bp long the isolated fragments were exposed to a ligation reaction before labelling with 32P-dCTP using either Prime-It random primer kit (Stratagene) or Ready to Go DNA labelling kit (Pharmacia).

3.7 RESULTS 3.7.1 Generation of PCR DNA fragments coding for α-1,4-glucan lyase.

The amino acid sequences (shown below) of three overlapping tryptic peptides from α-1,4-glucan lyase were used to generate mixed oligonucleotides, which could be used as PCR primers for amplification of DNA isolated from both MC and MV.

Lys Asn Leu His Pro Gln His Lys Met Leu Lys Asp Thr Val Leu Asp Ile Val Lys Pro Gly His Gly Glu Tyr Val Gly Trp Gly Glu Met Gly Gly Ile Gln Phe Met Lys Glu Pro Thr Phe Met Asn Tyr Phe Asn Phe Asp Asn Met Gln Tyr Gln Gln Val Tyr Ala Gln Gly Ala Leu Asp Ser Arg Glu Pro Leu Tyr His Ser Asp Pro Phe Tyr SEQ ID NO: 5.

In the first PCR amplification primers A1/A2 (see below) were used as upstream primers and primers B1/B2 (see below) were used as downstream primer.

Primer A1: CA(GA)CA(CT)AA(GA)ATGCT(GATC)AA(GA)GA(CT)AC SEQ ID NO: 6

Primer A2: CA(GA)CA(CT)AA(GA)ATGTT(GA)AA(GA)GA(CT)AC SEQ ID NO: 7

Primer B1: TA(GA)AA(GATC)GG(GA)TC(GA)CT(GA)TG(GA)TA SEQ ID NO: 8

Primer B2: TA(GA)AA(GATC)GG(GA)TC(GATC)GA(GA)TG(GA)TA SEQ ID NO: 9

The PCR products were analysed on a 2% LMT agarose gel and fragments of the expected sizes were cut out from the gel and treated with Agarase (Boehringer Manheim) and cloned into the pT7blue Vector (Novagen) and sequenced.

The cloned fragments from the PCR amplification coded for amino acids corresponding to the sequenced peptides (see above) and in each case in addition to two intron sequences. For MC the PCR amplified DNA sequence corresponds to the sequence shown as from position 1202 to position 1522 with reference to FIG. 4. For MV the PCR amplified DNA sequence corresponds to the sequence shown as from position 1218 to position 1535 with reference to FIG. 5.

3.7.2 Screening of the genomic libraries with the cloned PCR fragments.

Screening of the libraries with the above-mentioned clone gave two clones for each source. For MC the two clones were combined to form the sequence shown in FIG. 4 (see below). For MV the two clones could be combined to form the sequence shown in FIG. 5 in the manner described above.

An additional PCR was performed to supplement the MC clone with PstI, PvuII, AscI and NcoI restriction sites immediately in front of the ATG start codon using the following oligonucleotide as an upstream primer:
AAACTGCAGCTGGCGCGCCATGGCAG-GATTTCTGAT SEQ ID NO: 10
and a primer containing the complement sequence of bp 1297–1318 in FIG. 4 was used as a downstream primer.

The complete sequence for MC was generated by cloning the 5' end of the gene as a BglII-EcoRI fragment from one of the genomic clone (first clone) into the BamHI-EcoRI sites of pBluescript II KS+vector from Stratagene. The 3' end of the gene was then cloned into the modified pBluescript II KS+vector by ligating an NspV (blunt ended, using the DNA blunting kit from Amersham International)-EcoRI fragment from the other genomic clone (second clone) after the modified pBluescript II KS+vector had been digested with EcoRI and EcoRV. Then the intermediate part of the gene was cloned in to the further modified pBluescript II KS+vector as an EcoRI fragment from the first clone by ligating that fragment into the further modified pBluescript II KS+vector digested with EcoRI.

4. EXPRESSION OF THE GL GENE IN MICROORGANISMS

The DNA sequence encoding the GL can be introduced into microorganisms to produce the enzyme with high specific activity and in large quantities.

In this regard, the MC gene (FIG. 4) was cloned as a XbaI-XhoI blunt ended (using the DNA blunting kit from Amersham International) fragment into the Pichia expression vector pHIL-D2 (containing the AOX1 promoter) digested with EcoRI and blunt ended (using the DNA blunting kit from Amersham International) for expression in *Pichia pastoris* (according to the protocol stated in the Pichia Expression Kit supplied by Invitrogen).

In another embodiment, the MC gene 1 (same as FIG. 4 except that it was modified by PCR to introduce restriction sites as described above) was cloned as a PvuII-XhoI blunt ended fragment (using the DNA blunting kit from Amersham International) into the Aspergillus expression vector pBARMTE1 (containing the methyl tryptophan resistance promoter from *Neuropera crassa*) digested with SmaI for expression in *Aspergillus niger* (Pall et al (1993) Fungal Genet Newslett. vol 40 pages 59–62). The protoplasts were prepared according to Daboussi et al (Curr Genet (1989) vol 15 pp (453–456) using lysing enzymes Sigma L-2773 and the lyticase Sigma L-8012. The transformation of the protoplasts was followed according to the protocol stated by Buxton et al (Gene (1985) vol 37 pp 207–214) except that for plating the transformed protoplasts the protocol laid out in Punt et al (Methods in Enzymology (1992) vol 216 pp 447–457) was followed but with the use of 0.6% osmotic stabilised top agarose.

The results showed that lyase activity was observed in the transformed *Pichia pastoris* and *Aspergillus niger*. These experiments are now described.

ANALYSES OF PICHIA LYASE TRANSFORMANTS AND ASPERGILLUS LYASE TRANSFORMANTS

GENERAL METHODS

Preparation of cell-free extracts.

The cells were harvested by centrifugation at 9000 rpm for 5 min and washed with 0.9% NaCl and resuspended in the breaking buffer (50 mM K-phosphate, pH 7.5 containing 1 mM of EDTA, and 5% glycerol). Cells were broken using glass beads and vortex treatment. The breaking buffer contained 1 mM PMSF (protease inhibitor). The lyase extract (supernatant) was obtained after centrifugation at 9000 rpm for 5 min followed by centrifugation at 20,000×g for 5 min. Assay of lyase activity by alkaline 3,5-dinitrosalicylic acid reagent (DNS)

One volume of lyase extract was mixed with an equal volume of 4% amylopectin solution. The reaction mixture was then incubated at a controlled temperature and samples vere removed at specified intervals and analyzed for AF.

The lyase activity was also analyzed using a radioactive method.

The reaction mixture contained 10 $\mu$l $^{14}$C-starch solution (1 $\mu$Ci; Sigma Chemicals Co.) and 10 $\mu$l of the lyase extract. The reaction mixture was left at 25° C. overnight and was then analyzed in the usual TLC system. The radioactive AF produced was detected using an Instant Imager (Pachard Instrument Co., Inc., Meriden, Conn.).
Electrophoresis and Western blotting SDS-PAGE was performed using 8–25% gradient gels and the PhastSystem (Pharmacia). Western blottings was also run on a Semidry transfer unit of the PhastSystem. Primary antibodies raised against the lyase purified from the red seaweed collected at Qingdao (China) were used in a dilution of 1:100. Pig antirabbit IgG conjugated to alkaline phosphatase (Dako A/S, Glostrup, Denmark) were used as secondary antibodies and used in a dilution of 1:1000.
Part I, Analysis of the Pichia transformantscontaining the above mentioned construct

| MC-Lyase expressed intracellularly in *Pichia pastoris* | |
|---|---|
| Names of culture | Specific activity* |
| A18 | 10 |
| A20 | 32 |
| A21 | 8 |
| A22 | 8 |
| A24 | 6 |

*The specific activity was defined as nmol of AF produced per min per mg protein at 25° C.

Part II, The Aspergilus transformants
Results
I. Lyase activity was determined after 5 days incubation (minimal medium containing 0.2% casein enzymatic hydrolysate analysis by the alkaline 3,5-dinitrosalicylic acid reagent

| Lyase activity analysis in cell-free extracts | |
|---|---|
| Name of the culture | Specific activity* |
| 8.13 | 11 |
| 8.16 | 538 |
| 8.19 | 37 |

*The specific activity was defined as nmol of AF produced per min per mg protein at 25° C.

The results show that the MC-lyase was expressed intracellular in *A. niger*.

Instead of *Aspergillus niger* as host, other industrial important nicroorganisms for which good expression systems are known could be used such as: *Aspergillus oryzae*, Aspergillus sp., Trichoderma sp., *Saccharomyces cerevisiae*, Kluyveromyces sp., Hansenula sp., Pichia sp., *Bacillus subtilis*, *B. amyloliquefaciens*, Bacillus sp., Streptomyces sp. or *E. coli*.

Other preferred embodiments of the present invention include any one of the following: A transformed host organism having the capability of producing AF as a consequence of the introduction of a DNA sequence as herein described; such a transformed host organism which is a microorganism—preferably wherein the host organism is selected from the group consisting of bacteria, moulds, fungi and yeast; preferably the host organism is selected from the group consisting of Saccharomyces, Kluyveromyces, Aspergillus, Trichoderma Hansenula, Pichia, Bacillus Streptomyces, Eschericia such as *Aspergillus oryzae, Saccharomyces cerevisiae, Bacillus sublilis, Bacillus amyloliquefascien, Eschericia coli.*; A method for preparing the sugar 1,5-D-anhydrofructose comprising contacting an alpha 1,4-glucan (e.g. starch) with the enzyme α-1,4-glucan lyase expressed by a transformed host organism comprising a nucleotide sequence encoding the same, preferably wherein the nucleotide sequence is a DNA sequence, preferably wherein the DNA sequence is one of the sequences hereinbefore described; A vector incorporating a nucleotide sequence as hereinbefore described, preferably wherein the vector is a replication vector, preferably wherein the vector is an expression vector containing the nucleotide sequence downstream from a promoter sequence, preferably the vector contains a marker (such as a resistance marker); Cellular organisms, or cell line, transformed with such a vector; A method of producing the product α-1,4-glucan lyase or any nucleotide sequence or part thereof coding for same, which comprises culturing such an organism (or cells from a cell line) transfected with such a vector and recovering the product.

Other modifications of the present invention will be apparent to those skilled in the art without departing from the scope of the invention.

We claim:

1. A method of preparing fungal α-1,4-glucan lyase comprising isolating α-1,4-glucan lyase from a culture of a fungus.

2. A method according to claim 1 wherein the α-1,4-glucan lyase is isolated and/or further purified using a gel that is not degraded by α-1,4-lyase.

3. A method according to claim 2 wherein the gel comprises dextrin.

4. A method according to claim 1, wherein the fungus is selected from the group consisting of *Morchella costata* or *Morchella vulgaris*.

5. An α-1,4-glucan lyase enzyme prepared by the method of claim 1.

6. An isolated fungal α-1,4-glucan lyase enzyme comprising an amino acid sequence selected from the group consisting of SEQ ID NO:1, SEQ ID NO:2, and any variant thereof, said enzyme being obtainable from a culture of a fungus.

7. An isolated polynucleotide fragment coding for fungal α-1,4-glucan lyase.

8. The isolated polynucleotide according to claim 7 wherein the polynucleotide comprises DNA.

9. An isolated polynucleotide according to claim 8 wherein the DNA comprises a sequence that is the same as, or is complementary to, or specifically hybridizes under stringent hybridization conditions with, or contains any suitable codon substitutions for any of those of, SEQ ID NO:3 or SEQ ID NO:4.

10. A method of preparing α-1,4-glucan lyase enzyme comprising the step of expressing in a biological system a polynucleotide having a sequence selected from the group consisting of SEQ ID NO:3 and SEQ ID NO:4.

11. A method according to claim 2, wherein the gel comprises a cyclodextrin.

12. A method according to claim 11, wherein the gel comprises beta-cyclodextrin.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 1066 amino acids
      (B) TYPE: amino acid
      (D) TOPOLOGY: linear (ii) MOLECULE TYPE: protein (xi) SEQUENCE DESCRIPTION: SEQ ID NO: 1:

```
Met Ala Gly Phe Ser Asp Pro Leu Asn Phe Cys Lys Ala Glu Asp Tyr
1               5                   10                  15

Tyr Ser Val Ala Leu Asp Trp Lys Gly Pro Gln Lys Ile Ile Gly Val
                20                  25                  30

Asp Thr Thr Pro Pro Lys Ser Thr Lys Phe Pro Lys Asn Trp His Gly
            35                  40                  45

Val Asn Leu Arg Phe Asp Asp Gly Thr Leu Gly Val Val Gln Phe Ile
        50                  55                  60

Arg Pro Cys Val Trp Arg Val Arg Tyr Asp Pro Gly Phe Lys Thr Ser
65                  70                  75                  80

Asp Glu Tyr Gly Asp Glu Asn Thr Arg Thr Ile Val Gln Asp Tyr Met
                85                  90                  95

Ser Thr Leu Ser Asn Lys Leu Asp Thr Tyr Arg Gly Leu Thr Trp Glu
                100                 105                 110

Thr Lys Cys Glu Asp Ser Gly Asp Phe Phe Thr Phe Ser Ser Lys Val
            115                 120                 125

Thr Ala Val Glu Lys Ser Glu Arg Thr Arg Asn Lys Val Gly Asp Gly
        130                 135                 140

Leu Arg Ile His Leu Trp Lys Ser Pro Phe Arg Ile Gln Val Val Arg
145                 150                 155                 160

Thr Leu Thr Pro Leu Lys Asp Pro Tyr Pro Ile Pro Asn Val Ala Ala
                165                 170                 175

Ala Glu Ala Arg Val Ser Asp Lys Val Val Trp Gln Thr Ser Pro Lys
                180                 185                 190

Thr Phe Arg Lys Asn Leu His Pro Gln His Lys Met Leu Lys Asp Thr
            195                 200                 205
```

-continued

```
Val Leu Asp Ile Val Lys Pro Gly His Gly Glu Tyr Val Gly Trp Gly
    210                 215                 220
Glu Met Gly Gly Ile Gln Phe Met Lys Glu Pro Thr Phe Met Asn Tyr
225                 230                 235                 240
Phe Asn Phe Asp Asn Met Gln Tyr Gln Gln Val Tyr Ala Gln Gly Ala
                245                 250                 255
Leu Asp Ser Arg Glu Pro Leu Tyr His Ser Asp Pro Phe Tyr Leu Asp
            260                 265                 270
Val Asn Ser Asn Pro Glu His Lys Asn Ile Thr Ala Thr Phe Ile Asp
        275                 280                 285
Asn Tyr Ser Gln Ile Ala Ile Asp Phe Gly Lys Thr Asn Ser Gly Tyr
    290                 295                 300
Ile Lys Leu Gly Thr Arg Tyr Gly Gly Ile Asp Cys Tyr Gly Ile Ser
305                 310                 315                 320
Ala Asp Thr Val Pro Glu Ile Val Arg Leu Tyr Thr Gly Leu Val Gly
                325                 330                 335
Arg Ser Lys Leu Lys Pro Arg Tyr Ile Leu Gly Ala His Gln Ala Cys
            340                 345                 350
Tyr Gly Tyr Gln Gln Glu Ser Asp Leu Tyr Ser Val Val Gln Gln Tyr
        355                 360                 365
Arg Asp Cys Lys Phe Pro Leu Asp Gly Ile His Val Asp Val Asp Val
    370                 375                 380
Gln Asp Gly Phe Arg Thr Phe Thr Thr Asn Pro His Thr Phe Pro Asn
385                 390                 395                 400
Pro Lys Glu Met Phe Thr Asn Leu Arg Asn Asn Gly Ile Lys Cys Ser
                405                 410                 415
Thr Asn Ile Thr Pro Val Ile Ser Ile Asn Asn Arg Glu Gly Gly Tyr
            420                 425                 430
Ser Thr Leu Leu Glu Gly Val Asp Lys Lys Tyr Phe Ile Met Asp Asp
        435                 440                 445
Arg Tyr Thr Glu Gly Thr Ser Gly Asn Ala Lys Asp Val Arg Tyr Met
    450                 455                 460
Tyr Tyr Gly Gly Gly Asn Lys Val Glu Val Asp Pro Asn Asp Val Asn
465                 470                 475                 480
Gly Arg Pro Asp Phe Lys Asp Asn Tyr Asp Phe Pro Ala Asn Phe Asn
                485                 490                 495
Ser Lys Gln Tyr Pro Tyr His Gly Gly Val Ser Tyr Gly Tyr Gly Asn
            500                 505                 510
Gly Ser Ala Gly Phe Tyr Pro Asp Leu Asn Arg Lys Glu Val Arg Ile
        515                 520                 525
Trp Trp Gly Met Gln Tyr Lys Tyr Leu Phe Asp Met Gly Leu Glu Phe
    530                 535                 540
Val Trp Gln Asp Met Thr Thr Pro Ala Ile His Thr Ser Tyr Gly Asp
545                 550                 555                 560
Met Lys Gly Leu Pro Thr Arg Leu Leu Val Thr Ser Asp Ser Val Thr
                565                 570                 575
Asn Ala Ser Glu Lys Lys Leu Ala Ile Glu Thr Trp Ala Leu Tyr Ser
            580                 585                 590
Tyr Asn Leu His Lys Ala Thr Trp His Gly Leu Ser Arg Leu Glu Ser
        595                 600                 605
Arg Lys Asn Lys Arg Asn Phe Ile Leu Gly Arg Gly Ser Tyr Ala Gly
    610                 615                 620
Ala Tyr Arg Phe Ala Gly Leu Trp Thr Gly Asp Asn Ala Ser Asn Trp
625                 630                 635                 640
```

-continued

```
Glu Phe Trp Lys Ile Ser Val Ser Gln Val Leu Ser Leu Gly Leu Asn
                645                 650                 655
Gly Val Cys Ile Ala Gly Ser Asp Thr Gly Gly Phe Glu Pro Tyr Arg
            660                 665                 670
Asp Ala Asn Gly Val Glu Glu Lys Tyr Cys Ser Pro Glu Leu Leu Ile
        675                 680                 685
Arg Trp Tyr Thr Gly Ser Phe Leu Leu Pro Trp Leu Arg Asn His Tyr
    690                 695                 700
Val Lys Lys Asp Arg Lys Trp Phe Gln Glu Pro Tyr Ser Tyr Pro Lys
705                 710                 715                 720
His Leu Glu Thr His Pro Glu Leu Ala Asp Gln Ala Trp Leu Tyr Lys
                725                 730                 735
Ser Val Leu Glu Ile Cys Arg Tyr Tyr Val Glu Leu Arg Tyr Ser Leu
            740                 745                 750
Ile Gln Leu Leu Tyr Asp Cys Met Phe Gln Asn Val Val Asp Gly Met
        755                 760                 765
Pro Ile Thr Arg Ser Met Leu Leu Thr Asp Thr Glu Asp Thr Thr Phe
    770                 775                 780
Phe Asn Glu Ser Gln Lys Phe Leu Asp Asn Gln Tyr Met Ala Gly Asp
785                 790                 795                 800
Asp Ile Leu Val Ala Pro Ile Leu His Ser Arg Lys Glu Ile Pro Gly
                805                 810                 815
Glu Asn Arg Asp Val Tyr Leu Pro Leu Tyr His Thr Trp Tyr Pro Ser
            820                 825                 830
Asn Leu Arg Pro Trp Asp Asp Gln Gly Val Ala Leu Gly Asn Pro Val
        835                 840                 845
Glu Gly Gly Ser Val Ile Asn Tyr Thr Ala Arg Ile Val Ala Pro Glu
    850                 855                 860
Asp Tyr Asn Leu Phe His Ser Val Val Pro Val Tyr Val Arg Glu Gly
865                 870                 875                 880
Ala Ile Ile Pro Gln Ile Glu Val Arg Gln Trp Thr Gly Gln Gly Gly
                885                 890                 895
Ala Asn Arg Ile Lys Phe Asn Ile Tyr Pro Gly Lys Asp Lys Glu Tyr
            900                 905                 910
Cys Thr Tyr Leu Asp Asp Gly Val Ser Arg Asp Ser Ala Pro Glu Asp
        915                 920                 925
Leu Pro Gln Tyr Lys Glu Thr His Glu Gln Ser Lys Val Glu Gly Ala
    930                 935                 940
Glu Ile Ala Lys Gln Ile Gly Lys Lys Thr Gly Tyr Asn Ile Ser Gly
945                 950                 955                 960
Thr Asp Pro Glu Ala Lys Gly Tyr His Arg Lys Val Ala Val Thr Gln
                965                 970                 975
Thr Ser Lys Asp Lys Thr Arg Val Thr Ile Glu Pro Lys His Asn
            980                 985                 990
Gly Tyr Asp Pro Ser Lys Glu Val Gly Asp Tyr Tyr Thr Ile Ile Leu
        995                 1000                1005
Trp Tyr Ala Pro Gly Phe Asp Gly Ser Ile Val Asp Val Ser Lys Thr
    1010                1015                1020
Thr Val Asn Val Glu Gly Gly Val Glu His Gln Val Tyr Lys Asn Ser
1025                1030                1035                1040
Asp Leu His Thr Val Val Ile Asp Val Lys Glu Val Ile Gly Thr Thr
                1045                1050                1055
```

-continued

```
Lys Ser Val Lys Ile Thr Cys Thr Ala Ala
            1060                1065
```

(2) INFORMATION FOR SEQ ID NO: 2:

(i) SEQUENCE CHARACTERISTICS:
       (A) LENGTH: 1070 amino acids
       (B) TYPE: amino acid
       (D) TOPOLOGY: linear (ii) MOLECULE TYPE: protein (xi) SEQUENCE DESCRIPTION: SEQ ID NO: 2:

```
Met Ala Gly Leu Ser Asp Pro Leu Asn Phe Cys Lys Ala Glu Asp Tyr
1               5                   10                  15

Tyr Ala Ala Lys Gly Trp Ser Gly Pro Gln Lys Ile Ile Arg Tyr
            20                  25                  30

Asp Gln Thr Pro Pro Gln Gly Thr Lys Asp Pro Lys Ser Trp His Ala
            35                  40                  45

Val Asn Leu Pro Phe Asp Asp Gly Thr Met Cys Val Val Gln Phe Val
50                  55                  60

Arg Pro Cys Val Trp Arg Val Arg Tyr Asp Pro Ser Val Lys Thr Ser
65                  70                  75                  80

Asp Glu Tyr Gly Asp Glu Asn Thr Arg Thr Ile Val Gln Asp Tyr Met
            85                  90                  95

Thr Thr Leu Val Gly Asn Leu Asp Ile Phe Arg Gly Leu Thr Trp Val
            100                 105                 110

Ser Thr Leu Glu Asp Ser Gly Glu Tyr Tyr Thr Phe Lys Ser Glu Val
            115                 120                 125

Thr Ala Val Asp Glu Thr Glu Arg Thr Arg Asn Lys Val Gly Asp Gly
            130                 135                 140

Leu Lys Ile Tyr Leu Trp Lys Asn Pro Phe Arg Ile Gln Val Val Arg
145                 150                 155                 160

Leu Leu Thr Pro Leu Val Asp Pro Phe Pro Ile Pro Asn Val Ala Asn
            165                 170                 175

Ala Thr Ala Arg Val Ala Asp Lys Val Val Trp Gln Thr Ser Pro Lys
            180                 185                 190

Thr Phe Arg Lys Asn Leu His Pro Gln His Lys Met Leu Lys Asp Thr
            195                 200                 205

Val Leu Asp Ile Ile Lys Pro Gly His Gly Glu Tyr Val Gly Trp Gly
            210                 215                 220

Glu Met Gly Gly Ile Glu Phe Met Lys Glu Pro Thr Phe Met Asn Tyr
225                 230                 235                 240

Phe Asn Phe Asp Asn Met Gln Tyr Gln Gln Val Tyr Ala Gln Gly Ala
            245                 250                 255

Leu Asp Ser Arg Glu Pro Leu Tyr His Ser Asp Pro Phe Tyr Leu Asp
            260                 265                 270

Val Asn Ser Asn Pro Glu His Lys Asn Ile Thr Ala Thr Phe Ile Asp
            275                 280                 285

Asn Tyr Ser Gln Ile Ala Ile Asp Phe Gly Lys Thr Asn Ser Gly Tyr
            290                 295                 300

Ile Lys Leu Gly Thr Arg Tyr Gly Gly Ile Asp Cys Tyr Gly Ile Ser
305                 310                 315                 320

Ala Asp Thr Val Pro Glu Ile Val Arg Leu Tyr Thr Gly Leu Val Gly
            325                 330                 335

Arg Ser Lys Leu Lys Pro Arg Tyr Ile Leu Gly Ala His Gln Ala Cys
            340                 345                 350
```

```
Tyr Gly Tyr Gln Gln Glu Ser Asp Leu His Ala Val Val Gln Gln Tyr
        355                 360                 365

Arg Asp Thr Lys Phe Pro Leu Asp Gly Leu His Val Asp Val Asp Phe
    370                 375                 380

Gln Asp Asn Phe Arg Thr Phe Thr Thr Asn Pro Ile Thr Phe Pro Asn
385                 390                 395                 400

Pro Lys Glu Met Phe Thr Asn Leu Arg Asn Asn Gly Ile Lys Cys Ser
                405                 410                 415

Thr Asn Ile Thr Pro Val Ile Ser Ile Arg Asp Arg Pro Asn Gly Tyr
            420                 425                 430

Ser Thr Leu Asn Glu Gly Tyr Asp Lys Lys Tyr Phe Ile Met Asp Asp
        435                 440                 445

Arg Tyr Thr Glu Gly Thr Ser Gly Asp Pro Gln Asn Val Arg Tyr Ser
    450                 455                 460

Phe Tyr Gly Gly Gly Asn Pro Val Glu Val Asn Pro Asn Asp Val Trp
465                 470                 475                 480

Ala Arg Pro Asp Phe Gly Asp Asn Tyr Asp Phe Pro Thr Asn Phe Asn
                485                 490                 495

Cys Lys Asp Tyr Pro Tyr His Gly Gly Val Ser Tyr Gly Tyr Gly Asn
            500                 505                 510

Gly Thr Pro Gly Tyr Tyr Pro Asp Leu Asn Arg Glu Val Arg Ile
        515                 520                 525

Trp Trp Gly Leu Gln Tyr Glu Tyr Leu Phe Asn Met Gly Leu Glu Phe
    530                 535                 540

Val Trp Gln Asp Met Thr Thr Pro Ala Ile His Ser Ser Tyr Gly Asp
545                 550                 555                 560

Met Lys Gly Leu Pro Thr Arg Leu Leu Val Thr Ala Asp Ser Val Thr
                565                 570                 575

Asn Ala Ser Glu Lys Lys Leu Ala Ile Glu Ser Trp Ala Leu Tyr Ser
            580                 585                 590

Tyr Asn Leu His Lys Ala Thr Phe His Gly Leu Gly Arg Leu Glu Ser
        595                 600                 605

Arg Lys Asn Lys Arg Asn Phe Ile Leu Gly Arg Gly Ser Tyr Ala Gly
    610                 615                 620

Ala Tyr Arg Phe Ala Gly Leu Trp Thr Gly Asp Asn Ala Ser Thr Trp
625                 630                 635                 640

Glu Phe Trp Lys Ile Ser Val Ser Gln Val Leu Ser Leu Gly Leu Asn
                645                 650                 655

Gly Val Cys Ile Ala Gly Ser Asp Thr Gly Phe Glu Pro Ala Arg
            660                 665                 670

Thr Glu Ile Gly Glu Glu Lys Tyr Cys Ser Pro Glu Leu Leu Ile Arg
        675                 680                 685

Trp Tyr Thr Gly Ser Phe Leu Leu Pro Trp Leu Arg Asn His Tyr Val
    690                 695                 700

Lys Lys Asp Arg Lys Trp Phe Gln Glu Pro Tyr Ala Tyr Pro Lys His
705                 710                 715                 720

Leu Glu Thr His Pro Glu Leu Ala Asp Gln Ala Trp Leu Tyr Lys Ser
                725                 730                 735

Val Leu Glu Ile Cys Arg Tyr Trp Val Glu Leu Arg Tyr Ser Leu Ile
            740                 745                 750

Gln Leu Leu Tyr Asp Cys Met Phe Gln Asn Val Val Asp Gly Met Pro
        755                 760                 765
```

```
Leu Ala Arg Ser Met Leu Leu Thr Asp Thr Glu Asp Thr Thr Phe Phe
    770                 775                 780
Asn Glu Ser Gln Lys Phe Leu Asp Asn Gln Tyr Met Ala Gly Asp Asp
785                 790                 795                 800
Ile Leu Val Ala Pro Ile Leu His Ser Arg Asn Glu Val Pro Gly Glu
                805                 810                 815
Asn Arg Asp Val Tyr Leu Pro Leu Phe His Thr Trp Tyr Pro Ser Asn
                820                 825                 830
Leu Arg Pro Trp Asp Asp Gln Gly Val Ala Leu Gly Asn Pro Val Glu
    835                 840                 845
Gly Gly Ser Val Ile Asn Tyr Thr Ala Arg Ile Val Ala Pro Glu Asp
    850                 855                 860
Tyr Asn Leu Phe His Asn Val Val Pro Val Tyr Ile Arg Glu Gly Ala
865                 870                 875                 880
Ile Ile Pro Gln Ile Gln Val Arg Gln Trp Ile Gly Glu Gly Gly Pro
                885                 890                 895
Asn Pro Ile Lys Phe Asn Ile Tyr Pro Gly Lys Asp Lys Glu Tyr Val
                900                 905                 910
Thr Tyr Leu Asp Asp Gly Val Ser Arg Asp Ser Ala Pro Asp Asp Leu
    915                 920                 925
Pro Gln Tyr Arg Glu Ala Tyr Glu Gln Ala Lys Val Glu Gly Lys Asp
    930                 935                 940
Val Gln Lys Gln Leu Ala Val Ile Gln Gly Asn Lys Thr Asn Asp Phe
945                 950                 955                 960
Ser Ala Ser Gly Ile Asp Lys Glu Ala Lys Gly Tyr His Arg Lys Val
                965                 970                 975
Ser Ile Lys Gln Glu Ser Lys Asp Lys Thr Arg Thr Val Thr Ile Glu
                980                 985                 990
Pro Lys His Asn Gly Tyr Asp Pro Ser Lys Glu Val Gly Asn Tyr Tyr
    995                 1000                1005
Thr Ile Ile Leu Trp Tyr Ala Pro Gly Phe Asp Gly Ser Ile Val Asp
    1010                1015                1020
Val Ser Gln Ala Thr Val Asn Ile Glu Gly Gly Val Glu Cys Glu Ile
1025                1030                1035                1040
Phe Lys Asn Thr Gly Leu His Thr Val Val Asn Val Lys Glu Val
                1045                1050                1055
Ile Gly Thr Thr Lys Ser Val Lys Ile Thr Cys Thr Thr Ala
                1060                1065                1070
```

(2) INFORMATION FOR SEQ ID NO: 3:

(i) SEQUENCE CHARACTERISTICS:
        (A) LENGTH: 3201 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
ATGGCAGGAT TTTCTGATCC TCTCAACTTT TGCAAAGCAG AAGACTACTA CAGTGTTGCG      60

CTAGACTGGA AGGGCCCTCA AAAATCATT GGAGTAGACA CTACTCCTCC AAAGAGCACC     120

AAGTTCCCCA AAAACTGGCA TGGAGTGAAC TTGAGATTCG ATGATGGGAC TTTAGGTGTG     180

GTTCAGTTCA TTAGGCCGTG CGTTTGGAGG GTTAGATACG ACCCTGGTTT CAAGACCTCT     240

GACGAGTATG GTGATGAGAA TACGAGGACA ATTGTGCAAG ATTATATGAG TACTCTGAGT     300
```

```
AATAAATTGG ATACTTATAG AGGTCTTACG TGGGAAACCA AGTGTGAGGA TTCGGGAGAT      360

TTCTTTACCT TCTCATCCAA GGTCACCGCC GTTGAAAAAT CCGAGCGGAC CCGCAACAAG      420

GTCGGCGATG GCCTCAGAAT TCACCTATGG AAAAGCCCTT TCCGCATCCA AGTAGTGCGC      480

ACCTTGACCC CTTTGAAGGA TCCTTACCCC ATTCCAAATG TAGCCGCAGC CGAAGCCCGT      540

GTGTCCGACA AGGTCGTTTG GCAAACGTCT CCCAAGACAT TCAGAAAGAA CCTGCATCCG      600

CAACACAAGA TGCTAAAGGA TACAGTTCTT GACATTGTCA AACCTGGACA TGGCGAGTAT      660

GTGGGGTGGG GAGAGATGGG AGGTATCCAG TTTATGAAGG AGCCAACATT CATGAACTAT      720

TTTAACTTCG ACAATATGCA ATACCAGCAA GTCTATGCCC AAGGTGCTCT CGATTCTCGC      780

GAGCCACTGT ACCACTCGGA TCCCTTCTAT CTTGATGTGA ACTCCAACCC GGAGCACAAG      840

AATATCACGG CAACCTTTAT CGATAACTAC TCTCAAATTG CCATCGACTT TGGAAAGACC      900

AACTCAGGCT ACATCAAGCT GGGAACCAGG TATGGTGGTA TCGATTGTTA CGGTATCAGT      960

GCGGATACGG TCCCGGAAAT TGTACGACTT TATACAGGTC TTGTTGGACG TTCAAAGTTG     1020

AAGCCCAGAT ATATTCTCGG GGCCCATCAA GCCTGTTATG GATACCAACA GGAAAGTGAC     1080

TTGTATTCTG TGGTCCAGCA GTACCGTGAC TGTAAATTTC CACTTGACGG GATTCACGTC     1140

GATGTCGATG TTCAGGACGG CTTCAGAACT TTCACCACCA ACCCACACAC TTTCCCTAAC     1200

CCCAAAGAGA TGTTTACTAA CTTGAGGAAT AATGGAATCA AGTGCTCCAC CAATATCACT     1260

CCTGTTATCA GCATTAACAA CAGAGAGGGT GGATACAGTA CCCTCCTTGA GGGAGTTGAC     1320

AAAAAATACT TTATCATGGA CGACAGATAT ACCGAGGGAA CAAGTGGGAA TGCGAAGGAT     1380

GTTCGGTACA TGTACTACGG TGGTGGTAAT AAGGTTGAGG TCGATCCTAA TGATGTTAAT     1440

GGTCGGCCAG ACTTTAAAGA CAACTATGAC TTCCCCGCGA ACTTCAACAG CAAACAATAC     1500

CCCTATCATG GTGGTGTGAG CTACGGTTAT GGGAACGGTA GTGCAGGTTT TTACCCGGAC     1560

CTCAACAGAA AGGAGGTTCG TATCTGGTGG GAATGCAGT ACAAGTATCT CTTCGATATG      1620

GGACTGGAAT TTGTGTGGCA AGACATGACT ACCCCAGCAA TCCACACATC ATATGGAGAC     1680

ATGAAAGGGT TGCCCACCCG TCTACTCGTC ACCTCAGACT CCGTCACCAA TGCCTCTGAG     1740

AAAAAGCTCG CAATTGAAAC TTGGGCTCTC TACTCCTACA ATCTCCACAA AGCAACTTGG     1800

CATGGTCTTA GTCGTCTCGA ATCTCGTAAG AACAAACGAA ACTTCATCCT CGGGCGTGGA     1860

AGTTATGCCG GAGCCTATCG TTTTGCTGGT CTCTGGACTG GGATAATGC AAGTAACTGG      1920

GAATTCTGGA AGATATCGGT CTCTCAAGTT CTTTCTCTGG GCCTCAATGG TGTGTGCATC     1980

GCGGGGTCTG ATACGGGTGG TTTTGAACCC TACCGTGATG CAAATGGGGT CGAGGAGAAA     2040

TACTGTAGCC CAGAGCTACT CATCAGGTGG TATACTGGTT CATTCCTCTT GCCGTGGCTC     2100

AGGAACCATT ATGTCAAAAA GGACAGGAAA TGGTTCCAGG AACCATACTC GTACCCCAAG     2160

CATCTTGAAA CCCATCCAGA ACTCGCAGAC CAAGCATGGC TCTATAAATC CGTTTTGGAG     2220

ATCTGTAGGT ACTATGTGGA GCTTAGATAC TCCCTCATCC AACTACTTTA CGACTGCATG     2280

TTTCAAAACG TAGTCGACGG TATGCCAATC ACCAGATCTA TGCTCTTGAC CGATACTGAG     2340

GATACCACCT TCTTCAACGA GAGCCAAAAG TTCCTCGACA ACCAATATAT GGCTGGTGAC     2400

GACATTCTTG TTGCACCCAT CCTCCACAGT CGCAAAGAAA TTCCAGGCGA AACAGAGAT      2460

GTCTATCTCC CTCTTTACCA CACCTGGTAC CCCTCAAATT TGAGACCATG GGACGATCAA     2520

GGAGTCGCTT TGGGGAATCC TGTCGAAGGT GGTAGTGTCA TCAATTATAC TGCTAGGATT     2580

GTTGCACCCG AGGATTATAA TCTCTTCCAC AGCGTGGTAC CAGTCTACGT TAGAGAGGGT     2640

GCCATCATCC CGCAAATCGA AGTACGCCAA TGGACTGGCC AGGGGGGAGC CAACCGCATC     2700
```

| | |
|---|---:|
| AAGTTCAACA TCTACCCTGG AAAGGATAAG GAGTACTGTA CCTATCTTGA TGATGGTGTT | 2760 |
| AGCCGTGATA GTGCGCCGGA AGACCTCCCA CAGTACAAAG AGACCCACGA ACAGTCGAAG | 2820 |
| GTTGAAGGCG CGGAAATCGC AAAGCAGATT GGAAAGAAGA CGGGTTACAA CATCTCAGGA | 2880 |
| ACCGACCCAG AAGCAAAGGG TTATCACCGC AAAGTTGCTG TCACACAAAC GTCAAAAGAC | 2940 |
| AAGACGCGTA CTGTCACTAT TGAGCCAAAA CACAATGGAT ACGACCCTTC CAAAGAGGTG | 3000 |
| GGTGATTATT ATACCATCAT TCTTTGGTAC GCACCAGGTT TCGATGGCAG CATCGTCGAT | 3060 |
| GTGAGCAAGA CGACTGTGAA TGTTGAGGGT GGGGTGGAGC ACCAAGTTTA TAAGAACTCC | 3120 |
| GATTTACATA CGGTTGTTAT CGACGTGAAG GAGGTGATCG GTACCACAAA GAGCGTCAAG | 3180 |
| ATCACATGTA CTGCCGCTTA A | 3201 |

(2) INFORMATION FOR SEQ ID NO: 4:

(i) SEQUENCE CHARACTERISTICS:
        (A) LENGTH: 3213 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

| | |
|---|---:|
| ATGGCAGGAT TATCCGACCC TCTCAATTTC TGCAAAGCAG AGGACTACTA CGCTGCTGCC | 60 |
| AAAGGCTGGA GTGGCCCTCA GAAGATCATT CGCTATGACC AGACCCCTCC TCAGGGTACA | 120 |
| AAAGATCCGA AAAGCTGGCA TGCGGTAAAC CTTCCTTTCG ATGACGGGAC TATGTGTGTA | 180 |
| GTGCAATTCG TCAGACCCTG TGTTTGGAGG GTTAGATATG ACCCCAGTGT CAAGACTTCT | 240 |
| GATGAGTACG GCGATGAGAA TACGAGGACT ATTGTACAAG ACTACATGAC TACTCTGGTT | 300 |
| GGAAACTTGG ACATTTTCAG AGGTCTTACG TGGGTTTCTA CGTTGGAGGA TTCGGGCGAG | 360 |
| TACTACACCT TCAAGTCCGA AGTCACTGCC GTGGACGAAA CCGAACGGAC TCGAAACAAG | 420 |
| GTCGGCGACG GCCTCAAGAT TTACCTATGG AAAAATCCCT TTCGCATCCA GGTAGTGCGT | 480 |
| CTCTTGACCC CCCTGGTGGA CCCTTTCCCC ATTCCCAACG TAGCCAATGC CACAGCCCGT | 540 |
| GTGGCCGACA AGGTTGTTTG GCAGACGTCC CCGAAGACGT TCAGGAAAAA CTTGCATCCG | 600 |
| CAGCATAAGA TGTTGAAGGA TACAGTTCTT GATATTATCA AGCCGGGGCA CGGAGAGTAT | 660 |
| GTGGGTTGGG GAGAGATGGG AGGCATCGAG TTTATGAAGG AGCCAACATT CATGAATTAT | 720 |
| TTCAACTTTG ACAATATGCA ATATCAGCAG GTCTATGCAC AAGGCGCTCT TGATAGTCGT | 780 |
| GAGCCGTTGT ATCACTCTGA TCCCTTCTAT CTCGACGTGA ACTCCAACCC AGAGCACAAG | 840 |
| AACATTACGG CAACCTTTAT CGATAACTAC TCTCAGATTG CCATCGACTT TGGGAAGACC | 900 |
| AACTCAGGCT ACATCAAGCT GGGTACCAGG TATGGCGGTA TCGATTGTTA CGGTATCAGC | 960 |
| GCGGATACGG TCCCGGAGAT TGTGCGACTT TATACTGGAC TTGTTGGGCG TTCGAAGTTG | 1020 |
| AAGCCCAGGT ATATTCTCGG AGCCCACCAA GCTTGTTATG GATACCAGCA GGAAAGTGAC | 1080 |
| TTGCATGCTG TTGTTCAGCA GTACCGTGAC ACCAAGTTTC CGCTTGATGG GTTGCATGTC | 1140 |
| GATGTCGACT TTCAGGACAA TTTCAGAACG TTTACCACTA ACCCGATTAC GTTCCCTAAT | 1200 |
| CCCAAAGAAA TGTTTACCAA TCTAAGGAAC AATGGAATCA AGTGTTCCAC CAACATCACC | 1260 |
| CCTGTTATCA GTATCAGAGA TCGCCCGAAT GGGTACAGTA CCCTCAATGA GGGATATGAT | 1320 |
| AAAAAGTACT TCATCATGGA TGACAGATAT ACCGAGGGGA CAAGTGGGGA CCCGCAAAAT | 1380 |
| GTTCGATACT CTTTTTACGG CGGTGGGAAC CCGGTTGAGG TTAACCCTAA TGATGTTTGG | 1440 |
| GCTCGGCCAG ACTTTGGAGA CAATTATGAC TTCCCTACGA ACTTCAACTG CAAAGACTAC | 1500 |

```
CCCTATCATG GTGGTGTGAG TTACGGATAT GGGAATGGCA CTCCAGGTTA CTACCCTGAC    1560

CTTAACAGAG AGGAGGTTCG TATCTGGTGG GGATTGCAGT ACGAGTATCT CTTCAATATG    1620

GGACTAGAGT TTGTATGGCA AGATATGACA ACCCCAGCGA TCCATTCATC ATATGGAGAC    1680

ATGAAAGGGT TGCCCACCCG TCTGCTCGTC ACCGCCGACT CAGTTACCAA TGCCTCTGAG    1740

AAAAAGCTCG CAATTGAAAG TTGGGCTCTT TACTCCTACA ACCTCCATAA AGCAACCTTC    1800

CACGGTCTTG GTCGTCTTGA GTCTCGTAAG AACAAACGTA ACTTCATCCT CGGACGTGGT    1860

AGTTACGCCG GTGCCTATCG TTTTGCTGGT CTCTGGACTG GAGATAACGC AAGTACGTGG    1920

GAATTCTGGA AGATTTCGGT CTCCCAAGTT CTTTCTCTAG GTCTCAATGG TGTGTGTATA    1980

GCGGGGTCTG ATACGGGTGG TTTTGAGCCC GCACGTACTG AGATTGGGGA GGAGAAATAT    2040

TGCAGTCCGG AGCTACTCAT CAGGTGGTAT ACTGGATCAT TCCTTTTGCC ATGGCTTAGA    2100

AACCACTACG TCAAGAAGGA CAGGAAATGG TTCCAGGAAC CATACGCGTA CCCCAAGCAT    2160

CTTGAAACCC ATCCAGAGCT CGCAGATCAA GCATGGCTTT ACAAATCTGT TCTAGAAATT    2220

TGCAGATACT GGGTAGAGCT AAGATATTCC CTCATCCAGC TCCTTTACGA CTGCATGTTC    2280

CAAAACGTGG TCGATGGTAT GCCACTTGCC AGATCTATGC TCTTGACCGA TACTGAGGAT    2340

ACGACCTTCT TCAATGAGAG CCAAAAGTTC CTCGATAACC AATATATGGC TGGTGACGAC    2400

ATCCTTGTAG CACCCATCCT CCACAGCCGT AACGAGGTTC CGGGAGAGAA CAGAGATGTC    2460

TATCTCCCTC TATTCCACAC CTGGTACCCC TCAAACTTGA GACCGTGGGA CGATCAGGGA    2520

GTCGCTTTAG GGAATCCTGT CGAAGGTGGC AGCGTTATCA ACTACACTGC CAGGATTGTT    2580

GCCCCAGAGG ATTATAATCT CTTCCACAAC GTGGTGCCGG TCTACATCAG AGAGGGTGCC    2640

ATCATTCCGC AAATTCAGGT ACGCCAGTGG ATTGGCGAAG GAGGGCCTAA TCCCATCAAG    2700

TTCAATATCT ACCCTGGAAA GGACAAGGAG TATGTGACGT ACCTTGATGA TGGTGTTAGC    2760

CGCGATAGTG CACCAGATGA CCTCCCGCAG TACCGCGAGG CCTATGAGCA AGCGAAGGTC    2820

GAAGGCAAAG ACGTCCAGAA GCAACTTGCG GTCATTCAAG GGAATAAGAC TAATGACTTC    2880

TCCGCCTCCG GGATTGATAA GGAGGCAAAG GGTTATCACC GCAAAGTTTC TATCAAACAG    2940

GAGTCAAAAG ACAAGACCCG TACTGTCACC ATTGAGCCAA ACACAACGG ATACGACCCC     3000

TCTAAGGAAG TTGGTAATTA TTATACCATC ATTCTTTGGT ACGCACCGGG CTTTGACGGC    3060

AGCATCGTCG ATGTGAGCCA GGCGACCGTG AACATCGAGG GCGGGGTGGA ATGCGAAATT    3120

TTCAAGAACA CCGGCTTGCA TACGGTTGTA GTCAACGTGA AAGAGGTGAT CGGTACCACA    3180

AAGTCCGTCA AGATCACTTG CACTACCGCT TAG                                 3213

(2) INFORMATION FOR SEQ ID NO: 5:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (xi) SEQUENCE DESCRIPTION: SEQ ID NO: 5:

Lys Asn Leu His Pro Gln His Lys Met Leu Lys Asp Thr Val Leu Asp
    1               5                   10                  15

Ile Val Lys Pro Gly His Gly Glu Tyr Val Gly Trp Gly Glu Met Gly
                    20                  25                  30

Gly Ile Gln Phe Met Lys Glu Pro Thr Phe Met Asn Tyr Phe Asn Phe
                35                  40                  45
```

```
Asp Asn Met Gln Tyr Gln Gln Val Tyr Ala Gln Gly Ala Leu Asp Ser
    50                  55                  60

Arg Glu Pro Leu Tyr His Ser Asp Pro Phe Tyr
 65              70                  75
```

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_difference
        (B) LOCATION: replace(3, "")
        (D) OTHER INFORMATION: /standard_name= "N is G or A"

(ix) FEATURE:
        (A) NAME/KEY: misc_difference
        (B) LOCATION: replace(6, "")
        (D) OTHER INFORMATION: /note= "N is C or T"

(ix) FEATURE:
        (A) NAME/KEY: misc_difference
        (B) LOCATION: replace(3, "")
        (D) OTHER INFORMATION: /note= "N is G or A"

(ix) FEATURE:
        (A) NAME/KEY: misc_difference
        (B) LOCATION: replace(9, "")
        (D) OTHER INFORMATION: /note= "N is G or A"

(ix) FEATURE:
        (A) NAME/KEY: misc_difference
        (B) LOCATION: replace(15, "")
        (D) OTHER INFORMATION: /note= "N is G or A or T or C"

(ix) FEATURE:
        (A) NAME/KEY: misc_difference
        (B) LOCATION: replace(18, "")
        (D) OTHER INFORMATION: /note= "N is G or A"

(ix) FEATURE:
        (A) NAME/KEY: misc_difference
        (B) LOCATION: replace(21, "")
        (D) OTHER INFORMATION: /note= "N is C or T"

(xi) SEQUENCE DESCRIPTION: SEQ ID NO: 6:

CANCANAANA TGCTNAANGA NAC                                                  23

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_difference
        (B) LOCATION: replace(3, "")
        (D) OTHER INFORMATION: /note= "N is G or A"

(ix) FEATURE:
        (A) NAME/KEY: misc_difference
        (B) LOCATION: replace(6, "")
        (D) OTHER INFORMATION: /note= "N is C or T"

(ix) FEATURE:
        (A) NAME/KEY: misc_difference
        (B) LOCATION: replace(9, "")

(D) OTHER INFORMATION: /note= "N is G or A"

(ix) FEATURE:
            (A) NAME/KEY: misc_difference
            (B) LOCATION: replace(15, "")
            (D) OTHER INFORMATION: /note= "N is G or A"

(ix) FEATURE:
            (A) NAME/KEY: misc_difference
            (B) LOCATION: replace(18, "")
            (D) OTHER INFORMATION: /note= "N is G or A"

(ix) FEATURE:
            (A) NAME/KEY: misc_difference
            (B) LOCATION: replace(21, "")
            (D) OTHER INFORMATION: /note= "N is C or T"

(xi) SEQUENCE DESCRIPTION: SEQ ID NO: 7:

CANCANAANA TGTTNAANGA NAC                                                        23

(2) INFORMATION FOR SEQ ID NO: 8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_difference
            (B) LOCATION: replace(3, "")
            (D) OTHER INFORMATION: /note= "N is G or A"

(ix) FEATURE:
            (A) NAME/KEY: misc_difference
            (B) LOCATION: replace(6, "")
            (D) OTHER INFORMATION: /note= "N is G or A or T or C"

(ix) FEATURE:
            (A) NAME/KEY: misc_difference
            (B) LOCATION: replace(9, "")
            (D) OTHER INFORMATION: /note= "N is G or A"

(ix) FEATURE:
            (A) NAME/KEY: misc_difference
            (B) LOCATION: replace(12, "")
            (D) OTHER INFORMATION: /note= "N is G or A"

(ix) FEATURE:
            (A) NAME/KEY: misc_difference
            (B) LOCATION: replace(15, "")
            (D) OTHER INFORMATION: /note= "N is G or A"

(ix) FEATURE:
            (A) NAME/KEY: misc_difference
            (B) LOCATION: replace(18, "")
            (D) OTHER INFORMATION: /note= "N is G or A"

(xi) SEQUENCE DESCRIPTION: SEQ ID NO: 8:

TANAANGGNT CNCTNTGNTA                                                            20

(2) INFORMATION FOR SEQ ID NO: 9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_difference
            (B) LOCATION: replace(3, "")

(D) OTHER INFORMATION: /note= "N is G or A"

(ix) FEATURE:
            (A) NAME/KEY: misc_difference
            (B) LOCATION: replace(6, "")
            (D) OTHER INFORMATION: /note= "N is G or A or T or C"

(ix) FEATURE:
            (A) NAME/KEY: misc_difference
            (B) LOCATION: replace(9, "")
            (D) OTHER INFORMATION: /note= "N is G or A"

(ix) FEATURE:
            (A) NAME/KEY: misc_difference
            (B) LOCATION: replace(12, "")
            (D) OTHER INFORMATION: /note= "N is G or A or T or C"

(ix) FEATURE:
            (A) NAME/KEY: misc_difference
            (B) LOCATION: replace(15, "")
            (D) OTHER INFORMATION: /note= "N is G or A"

(ix) FEATURE:
            (A) NAME/KEY: misc_difference
            (B) LOCATION: replace(18, "")
            (D) OTHER INFORMATION: /note= "N is G or A"

(xi) SEQUENCE DESCRIPTION: SEQ ID NO: 9:

TANAANGGNT CNGANTGNTA                                                    20

(2) INFORMATION FOR SEQ ID NO: 10:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 10:

AAACTGCAGC TGGCGCGCCA TGGCAGGATT TTCTGAT                                  37

(2) INFORMATION FOR SEQ ID NO:11:

(i) SEQUENCE CHARACTERISTICS:
            (A) LENGTH: 4726 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

AGACAGGTGC GTTTTTGTTT ATTCTATTCT GTGCGGCAGA TATGCACTCA CAAGAAACAA           60

ATTGTACAAA TATTTCTAAT TACAGTTGTA GGTGCAGTTG AAAATCCGGT CGCACAAAGA          120

TCATTGATGC ACAAAGATGA TAACGCCTGA TTAGTACTCA AGGTTTAATT GGGTATGTGT          180

GCGACCTCTC TTTGGCTAGC ATTACCTGAT TGGTTACAAC TGCAAATACT GCGGCAGCAA          240

TGAGGAATGA AGTCAGCATC GATAGCTCGG CCTCATAAAA ATTGATTTCA ATTTTATATT          300

CCCAGTTTTA ATCTCGAATC CTATATAATG GCCATCGTTC CCTCCTCGCC TCTTCATTCT          360

CCTCCATCAC TCCAGCTCAG TCATCCCTCA ACTTGGCCTC CTCTGATATC TTCCGAACAA          420

AACATCTTGT CCAATCTTTT TTTGAGCTAG ATCTCATTAT ACCTCCGTCA TGGCAGGATT          480

TTCTGATCCT CTCAACTTTT GCAAAGCAGA AGACTACTAC AGTGTTGCGC TAGACTGGAA          540

GGGCCCTCAA AAAATCATTG GAGTAGACAC TACTCCTCCA AAGAGCACCA AGTTCCCCAA          600

AAACTGGCAT GGAGTGAACT TGAGATTCGA TGATGGGACT TTAGGTGTGG TTCAGTTCAT          660

```
TAGGCCGTGC GTTTGGAGGG TTAGATACGA CCCTGGTTTC AAGACCTCTG ACGAGTATGG    720

TGATGAGAAT ACGTGAGTTA CCCCATATGT CATTATTGGT AGCGAAAAAC ATATGCTAAT    780

CAACTAACGA GGCATATAGG AGGACAATTG TGCAAGATTA TATGAGTACT CTGAGTAATA    840

AATTGGATAC TTATAGAGGT CTTACGTGGG AAACCAAGTG TGAGGATTCG GGAGATTTCT    900

TTACCTTCTC AGTAAGTGCC AGTACTGCTA TAGCTCCGCT ATATATATAA CACCACTAAC    960

TAACTGCCCT AAATAGTCCA AGGTCACCGC CGTTGAAAAA TCCGAGCGGA CCCGCAACAA   1020

GGTCGGCGAT GGCCTCAGAA TTCACCTATG GAAAAGCCCT TTCCGCATCC AAGTAGTGCG   1080

CACCTTGACC CCTTTGAAGG ATCCTTACCC CATTCCAAAT GTAGCCGCAG CCGAAGCCCG   1140

TGTGTCCGAC AAGGTCGTTT GGCAAACGTC TCCCAAGACA TTCAGAAAGA ACCTGCATCC   1200

GCAACACAAG ATGCTAAAGG ATACAGTTCT TGACATTGTC AAACCTGGAC ATGGCGAGTA   1260

TGTGGGGTGG GGAGAGATGG GAGGTATCCA GTTTATGAAG GAGCCAACAT TCATGAACTA   1320

TTTTAGTAAG CCCCGAAGAG GTTCCTTATA AATTCTTGGT GGTCATTTTT ACTAACCCAG   1380

TGTAGACTTC GACAATATGC AATACCAGCA AGTCTATGCC CAAGGTGCTC TCGATTCTCG   1440

CGAGCCACTG TAAGTACCGT CCTGTGGCAC GACTTAACCC AATAACTAAT CTTTCAACAA   1500

GGTACCACTC GGATCCCTTC TATCTTGATG TGAACTCCAA CCCGGAGCAC AAGAATATCA   1560

CGGCAACCTT TATCGATAAC TACTCTCAAA TTGCCATCGA CTTTGGAAAG ACCAACTCAG   1620

GCTACATCAA GCTGGGAACC AGGTATGGTG GTATCGATTG TTACGGTATC AGTGCGGATA   1680

CGGTCCCGGA AATTGTACGA CTTTATACAG GTCTTGTTGG ACGTTCAAAG TTGAAGCCCA   1740

GATATATTCT CGGGGCCCAT CAAGCCTGTA AGTCCTTCCC CTCATGAGTG ATTTATCAGA   1800

CTTGCATAAT AAACTAACCT CGTTTTCAAA GGTTATGGAT ACCAACAGGA AAGTGACTTG   1860

TATTCTGTGG TCCAGCAGTA CCGTGACTGT AAATTTCCAC TTGACGGGAT TCACGTCGAT   1920

GTCGATGTTC AGGTAAATGG CCATGGTATC ATTGAAGCTT TGAGAAATGT TCTAACTGTG   1980

TTTATAACAT TCCTAGGACG GCTTCAGAAC TTTCACCACC AACCCACACA CTTTCCCTAA   2040

CCCCAAAGAG ATGTTTACTA ACTTGAGGAA TAATGGAATC AAGTGCTCCA CCAATATCAC   2100

TCCTGTTATC AGCATTAACA ACAGAGAGGG TGGATACAGT ACCCTCCTTG AGGGAGTTGA   2160

CAAAAAATAC TTTATCATGG ACGACAGATA TACCGAGGGA ACAAGTGGGA ATGCGAAGGA   2220

TGTTCGGTAC ATGTACTACG GTGGTGGTAA TAAGGTTGAG GTCGATCCTA ATGATGTTAA   2280

TGGTCGGCCA GACTTTAAAG ACAACTAGTA AGTTGTTTAT TTGACTACGA TAGGTAACCC   2340

GTAAGCGGCA TTAACATATT TGTAGTGACT TCCCCGCGAA CTTCAACAGC AAACAATACC   2400

CCTATCATGG TGGTGTGAGC TACGGTTATG GGAACGGTAG TGTAAGTGAC GATATCTCAC   2460

CAACATAATG AAATTTATAA GGACTAACTA GACACAAAAA TTTGTAGGCA GGTTTTTACC   2520

CGGACCTCAA CAGAAAGGAG GTTCGTATCT GGTGGGAAT GCAGTACAAG TATCTCTTCG   2580

ATATGGGACT GGAATTTGTG TGGCAAGACA TGACTACCCC AGCAATCCAC ACATCATATG   2640

GAGACATGAA AGGGTTGCCC ACCCGTCTAC TCGTCACCTC AGACTCCGTC ACCAATGCCT   2700

CTGAGAAAAA GCTCGCAATT GAAACTTGGG CTCTCTACTC CTACAATCTC CACAAAGCAA   2760

CTTGGCATGG TCTTAGTCGT CTCGAATCTC GTAAGAACAA ACGAAACTTC ATCCTCGGGC   2820

GTGGAAGTTA TGCCGGAGCC TATCGTTTTG CTGGTCTCTG GACTGGGGAT AATGCAAGTA   2880

ACTGGGAATT CTGGAAGATA TCGTCTCTC AAGTTCTTTC TCTGGGCCTC AATGGTGTGT   2940

GCATCGCGGG GTCTGATACG GGTGGTTTTG AACCCTACCG TGATGCAAAT GGGGTCGAGG   3000

AGAAATACTG TAGCCCAGAG CTACTCATCA GGTGGTATAC TGGTTCATTC CTCTTGCCGT   3060
```

```
GGCTCAGGAA CCATTATGTC AAAAAGGACA GGAAATGGTT CCAGGTAATC TATCCTTTCT    3120

TATCTTTGAA GCATTGAAGA TACTAAGATA TAATCTAGGA ACCATACTCG TACCCCAAGC    3180

ATCTTGAAAC CCATCCAGAA CTCGCAGACC AAGCATGGCT CTATAAATCC GTTTTGGAGA    3240

TCTGTAGGTA CTATGTGGAG CTTAGATACT CCCTCATCCA ACTACTTTAC GACTGCATGT    3300

TTCAAAACGT AGTCGACGGT ATGCCAATCA CCAGATCTAT GGTATGTATT CTACCCTAGG    3360

CTTCCAGAGC AACATATGCT AACCAATTGA ACCTGGGTTT CTAGCTCTTG ACCGATACTG    3420

AGGATACCAC CTTCTTCAAC GAGAGCCAAA AGTTCCTCGA CAACCAATAT ATGGCTGGTG    3480

ACGACATTCT TGTTGCACCC ATCCTCCACA GTCGCAAAGA AATTCCAGGC GAAAACAGAG    3540

ATGTCTATCT CCCTCTTTAC CACACCTGGT ACCCCTCAAA TTTGAGACCA TGGGACGATC    3600

AAGGAGTCGC TTTGGGGAAT CCTGTCGAAG GTGGTAGTGT CATCAATTAT ACTGCTAGGA    3660

TTGTTGCACC CGAGGATTAT AATCTCTTCC ACAGCGTGGT ACCAGTCTAC GTTAGAGAGG    3720

GTAAGCAGTA AAATAATCTC TTCCCAGTTT CAAATACATT TAGCTAGTAG CTAACGCTAT    3780

GAACCTACAG GTGCCATCAT CCCGCAAATC GAAGTACGCC AATGGACTGG CCAGGGGGA    3840

GCCAACCGCA TCAAGTTCAA CATCTACCCT GGAAAGGATA AGGTAAAATT CAATGATCAC    3900

CCTGCATCTA TTCCATCGCT GGTTTTCTTT ACCCTTACTG ACTTCATTCC TCAAAATACA    3960

GGAGTACTGT ACCTATCTTG ATGATGGTGT TAGCCGTGAT AGTGCGCCGG AAGACCTCCC    4020

ACAGTACAAA GAGACCCACG AACAGTCGAA GGTTGAAGGC GCGGAAATCG CAAAGCAGAT    4080

TGGAAAGAAG ACGGGTTACA ACATCTCAGG AACCGACCCA GAAGCAAAGG GTTATCACCG    4140

CAAAGTTGCT GTCACACAAG TAATACCGCC CTTGACTTGT ATCACTTCCT GACATCATGC    4200

TAATATTTCT CTGTTTACCT CAAAGACGTC AAAAGACAAG ACGCGTACTG TCACTATTGA    4260

GCCAAAACAC AATGGATACG ACCCTTCCAA AGAGGTGGGT GATTATTATA CCATCATTCT    4320

TTGGTACGCA CCAGGTTTCG ATGGCAGCAT CGTCGATGTG AGCAAGACGA CTGTGAATGT    4380

TGAGGGTGGG GTGGAGCACC AAGTTTATAA GAACTCCGAT TTACATACGG TTGTTATCGA    4440

CGTGAAGGAG GTGATCGGTA CCACAAAGAG CGTCAAGATC ACATGTACTG CCGCTTAAGG    4500

TCTTTTCTTG GGGGCGGGAG GCGAGACCTT CGAAATGTAT ACGGGAGTGG TAACTCCGGG    4560

AAAATGGTGA TATGGGGAT CAAGTTGGAG GGGAATCTGT TTATTCTTT ATTTCTTTAT    4620

TTACTGGATT GGAAAATAGG GAGCACAGTT CTGACTGGAT TGGTTTGATT GTTGGCCTCT    4680

ACGGGTTCTC TTTACTTTGT CTGGAAATCC AATTTATTGT TATGCG                 4726
```

(2) INFORMATION FOR SEQ ID NO:12:

(i) SEQUENCE CHARACTERISTICS:
        (A) LENGTH: 4670 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
ATGCAGGCAA CGACAGGCGT TTTTTGTTTT ATCCGCAGAG GTGCAGCAGC AGGAAACAAA      60

CCATACAAAC ATTCCTTGAC GCGGTTTTAG GTGCAGTTAA GGCCCGGGCG CACCAAGAAC     120

ATTGATGTAC TTGGTCTAAA AAAGATCATA ATACCCGATT AGTGTTCATG GTTTGATTGG     180

GTCTAAGTAC AAGTTTTACA GAGTTCAGCT TAGTTCATTG TTCGAAACTA CCAATATCAC     240

ACCTATGCCT GCTGGCATTG ATAGCTCGGC TTGTGAAAGC TGATTACAAT CTTACATTTC     300
```

```
TGATTTAATA TCGGACTGAT CTATATATAA GGGTCATCAT TTCCTCTCCG CCTTTTGGTT      360

CTCTTTCATC ACCCCAGCCC AATCATCACC GTTGGCCTTT ACTTCTCTCT TCCGTTGATA      420

TTTTCTCGAC AAAACATCTT GTCCACTGTT AGGCTAGCTC CCAGAATTAT CCCTCCAACA      480

TGGCAGGATT ATCCGACCCT CTCAATTTCT GCAAAGCAGA GGACTACTAC GCTGCTGCCA      540

AAGGCTGGAG TGGCCCTCAG AAGATCATTC GCTATGACCA GACCCCTCCT CAGGGTACAA      600

AAGATCCGAA AAGCTGGCAT GCGGTAAACC TTCCTTTCGA TGACGGGACT ATGTGTGTAG      660

TGCAATTCGT CAGACCCTGT GTTTGGAGGG TTAGATATGA CCCCAGTGTC AAGACTTCTG      720

ATGAGTACGG CGATGAGAAT ACGTGGGTCG CCCAGTCAAT TAACTATGCC GCTAGTGATT      780

ATGGAAAGCT TCTGCTAACC GATCAATGAG GCATGTAGGA GGACTATTGT ACAAGACTAC      840

ATGACTACTC TGGTTGGAAA CTTGGACATT TTCAGAGGTC TTACGTGGGT TTCTACGTTG      900

GAGGATTCGG GCGAGTACTA CACCTTCAAG GCAAGCCTCA GTGTTATATC TCGAATATAT      960

TATATATCAC AACAAACTAA CTAGTCATAC AGTCCGAAGT CACTGCCGTG GACGAAACCG     1020

AACGGACTCG AAACAAGGTC GGCGACGGCC TCAAGATTTA CCTATGGAAA AATCCCTTTC     1080

GCATCCAGGT AGTGCGTCTC TTGACCCCCC TGGTGGACCC TTTCCCCATT CCCAACGTAG     1140

CCAATGCCAC AGCCCGTGTG GCCGACAAGG TTGTTTGGCA GACGTCCCCG AAGACGTTCA     1200

GGAAAAACTT GCATCCGCAG CATAAGATGT TGAAGGATAC AGTTCTTGAT ATTATCAAGC     1260

CGGGGCACGG AGAGTATGTG GGTTGGGGAG AGATGGGAGG CATCGAGTTT ATGAAGGAGC     1320

CAACATTCAT GAATTATTTC AGTAAGCTCT TGAAAGATTT CCTATCTCTT GACGGTCGTT     1380

TTTGCTAAGG AAACTGTAGA CTTTGACAAT ATGCAATATC AGCAGGTCTA TGCACAAGGC     1440

GCTCTTGATA GTCGTGAGCC GTTGTAAGTA ACGTCCTGTG ACATGTCATG ATTACAGTAA     1500

CTGATCGTTC AATAAGGTAT CACTCTGATC CCTTCTATCT CGACGTGAAC TCCAACCCAG     1560

AGCACAAGAA CATTACGGCA ACCTTTATCG ATAACTACTC TCAGATTGCC ATCGACTTTG     1620

GGAAGACCAA CTCAGGCTAC ATCAAGCTGG GTACCAGGTA TGGCGGTATC GATTGTTACG     1680

GTATCAGCGC GGATACGGTC CCGGAGATTG TGCGACTTTA TACTGGACTT GTTGGGCGTT     1740

CGAAGTTGAA GCCCAGGTAT ATTCTCGGAG CCCACCAAGC TTGTAAGCCC GCCCCCTTTA     1800

CGATGCATTT ATTAGGGGTC CACAGACTAA ACTTGTTCCA AAGGTTATGG ATACCAGCAG     1860

GAAAGTGACT TGCATGCTGT TGTTCAGCAG TACCGTGACA CCAAGTTTCC GCTTGATGGG     1920

TTGCATGTCG ATGTCGACTT TCAGGTAAAT GGCCCAGGTA TCGTTGAAGC TTTGGAGAAT     1980

GCTAATTGTG CTCGTAAAAC TTTAAGGACA ATTTCAGAAC GTTTACCACT AACCCGATTA     2040

CGTTCCCTAA TCCCAAAGAA ATGTTTACCA ATCTAAGGAA CAATGGAATC AAGTGTTCCA     2100

CCAACATCAC CCCTGTTATC AGTATCAGAG ATCGCCCGAA TGGGTACAGT ACCCTCAATG     2160

AGGGATATGA TAAAAAGTAC TTCATCATGG ATGACAGATA TACCGAGGGG ACAAGTGGGG     2220

ACCCGCAAAA TGTTCGATAC TCTTTTTACG GCGGTGGGAA CCCGGTTGAG GTTAACCCTA     2280

ATGATGTTTG GGCTCGGCCA GACTTTGGAG ACAATTAGTA AGTTACTCAA TAGGCTACTT     2340

GAGATATTCT GTAGGTGGCA TTAACACGAC TATAGTGACT TCCCTACGAA CTTCAACTGC     2400

AAAGACTACC CCTATCATGG TGGTGTGAGT TACGGATATG GAATGGCAC TGTAAGTGAT      2460

AATAAGTCAT AAATACAACG TAATTCATGG AGACTAATCA GTGGTAAATG AATTTTAGCC     2520

AGGTTACTAC CCTGACCTTA ACAGAGAGGA GGTTCGTATC TGGTGGGGAT TGCAGTACGA     2580

GTATCTCTTC AATATGGGAC TAGAGTTTGT ATGGCAAGAT ATGACAACCC CAGCGATCCA     2640

TTCATCATAT GGAGACATGA AAGGGTTGCC CACCCGTCTG CTCGTCACCG CCGACTCAGT     2700
```

```
TACCAATGCC TCTGAGAAAA AGCTCGCAAT TGAAAGTTGG GCTCTTTACT CCTACAACCT    2760

CCATAAAGCA ACCTTCCACG GTCTTGGTCG TCTTGAGTCT CGTAAGAACA AACGTAACTT    2820

CATCCTCGGA CGTGGTAGTT ACGCCGGTGC CTATCGTTTT GCTGGTCTCT GGACTGGAGA    2880

TAACGCAAGT ACGTGGGAAT TCTGGAAGAT TTCGGTCTCC CAAGTTCTTT CTCTAGGTCT    2940

CAATGGTGTG TGTATAGCGG GGTCTGATAC GGGTGGTTTT GAGCCCGCAC GTACTGAGAT    3000

TGGGGAGGAG AAATATTGCA GTCCGGAGCT ACTCATCAGG TGGTATACTG GATCATTCCT    3060

TTTGCCATGG CTTAGAAACC ACTACGTCAA GAAGGACAGG AAATGGTTCC AGGTAATATA    3120

CTCTTTCTGG TCTCTGAGTA TCGAAGACGC TAAGACAATA TAGGAACCAT ACGCGTACCC    3180

CAAGCATCTT GAAACCCATC CAGAGCTCGC AGATCAAGCA TGGCTTTACA AATCTGTTCT    3240

AGAAATTTGC AGATACTGGG TAGAGCTAAG ATATTCCCTC ATCCAGCTCC TTTACGACTG    3300

CATGTTCCAA AACGTGGTCG ATGGTATGCC ACTTGCCAGA TCTATGGTAT GCATTTTATC    3360

CGTCTCCTTT CACGATAATG CACCAGTCTA ACCGAATTTT CTTTTAGCTC TTGACCGATA    3420

CTGAGGATAC GACCTTCTTC AATGAGAGCC AAAAGTTCCT CGATAACCAA TATATGGCTG    3480

GTGACGACAT CCTTGTAGCA CCCATCCTCC ACAGCCGTAA CGAGGTTCCG GGAGAGAACA    3540

GAGATGTCTA TCTCCCTCTA TTCCACACCT GGTACCCCTC AAACTTGAGA CCGTGGGACG    3600

ATCAGGGAGT CGCTTTAGGG AATCCTGTCG AAGGTGGCAG CGTTATCAAC TACACTGCCA    3660

GGATTGTTGC CCCAGAGGAT TATAATCTCT TCCACAACGT GGTGCCGGTC TACATCAGAG    3720

AGGGTAAGCG ATGGAATAAT TTCTTGCAAG TTCCAGATAC AAGTGGTTAC TGACACCTTA    3780

AACCAGGTGC CATCATTCCG CAAATTCAGG TACGCCAGTG GATTGGCGAA GGAGGGCCTA    3840

ATCCCATCAA GTTCAATATC TACCCTGGAA AGGACAAGGT ATATTCTCCA TGACTATCGC    3900

GCATTTATTC TTTCTCTACT CGCACTAACT TCATCTGAAT ATAGGAGTAT GTGACGTACC    3960

TTGATGATGG TGTTAGCCGC GATAGTGCAC CAGATGACCT CCCGCAGTAC CGCGAGGCCT    4020

ATGAGCAAGC GAAGGTCGAA GGCAAAGACG TCCAGAAGCA ACTTGCGGTC ATTCAAGGGA    4080

ATAAGACTAA TGACTTCTCC GCCTCCGGGA TTGATAAGGA GGCAAAGGGT TATCACCGCA    4140

AAGTTTCTAT CAAACAGGTA CATGATTTCA TCTTCCTTTT TTCGCAGTCA CTATTATATC    4200

ATCCTAACAT TGCTTCTCTT ATTTAAAAGG AGTCAAAAGA CAAGACCCGT ACTGTCACCA    4260

TTGAGCCAAA ACACAACGGA TACGACCCCT CTAAGGAAGT TGGTAATTAT TATACCATCA    4320

TTCTTTGGTA CGCACCGGGC TTTGACGGCA GCATCGTCGA TGTGAGCCAG GCGACCGTGA    4380

ACATCGAGGG CGGGGTGGAA TGCGAAATTT TCAAGAACAC CGGCTTGCAT ACGGTTGTAG    4440

TCAACGTGAA AGAGGTGATC GGTACCACAA AGTCCGTCAA GATCACTTGC ACTACCGCTT    4500

AGAGCTCTTT TATGAGGGGT ATATGGGAGT GGCAGCTCAG AAATTTGGGA AGCTTCTGGG    4560

TATTCCTTTT GTTTATTTAC TTATTTATTG AATCGACCAA TACGGGTGGG ATTCTCTCTG    4620

GTTTTTGTGA GGCTATGTTT TACTTGGTCT GAAAATCAAA TTCGTTCTCA              4670
```